(12) United States Patent
Robinson et al.

(10) Patent No.: US 7,285,570 B2
(45) Date of Patent: Oct. 23, 2007

(54) COMPOSITIONS AND METHODS FOR REGULATING MAMMALIAN KERATINOUS TISSUE

(75) Inventors: Larry Richard Robinson, Loveland, OH (US); Paul Robert Tanner, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 505 days.

(21) Appl. No.: 10/418,594

(22) Filed: Apr. 17, 2003

(65) Prior Publication Data

US 2004/0208903 A1  Oct. 21, 2004

(51) Int. Cl.
*A61K 31/40* (2006.01)

(52) U.S. Cl. .................. 514/423; 424/400; 424/401

(58) Field of Classification Search ............... None
See application file for complete search history.

(56) References Cited

U.S. PATENT DOCUMENTS

| | | | | |
|---|---|---|---|---|
| 4,208,421 | A | * | 6/1980 | Morelle et al. ............. 514/423 |
| 4,505,924 | A | | 3/1985 | Taylor et al. |
| 4,559,054 | A | | 12/1985 | Bruck |
| 5,093,109 | A | | 3/1992 | Mausner |
| 5,100,674 | A | | 3/1992 | Ser et al. |
| 5,601,833 | A | * | 2/1997 | Ribier et al. ................ 424/401 |
| 5,614,178 | A | | 3/1997 | Bloom et al. |
| 5,679,374 | A | | 10/1997 | Franchon et al. |
| 5,690,918 | A | * | 11/1997 | Jacks et al. ................... 424/64 |
| 5,716,800 | A | | 2/1998 | Meybeck et al. |
| 6,153,209 | A | | 11/2000 | Vega et al. |
| 6,207,596 | B1 | | 3/2001 | Rourke et al. |
| 6,238,682 | B1 | | 5/2001 | Klofta et al. |
| 6,344,218 | B1 | | 2/2002 | Dodd et al. |
| 6,451,850 | B1 | | 9/2002 | Solovieu et al. |
| 6,570,054 | B1 | | 5/2003 | Gatto et al. |
| 2002/0028222 | A1 | | 3/2002 | Alfriat et al. |
| 2002/0034480 | A1 | | 3/2002 | Grimm et al. |
| 2002/0041854 | A1 | | 4/2002 | Hadasch et al. |
| 2002/0058010 | A1 | | 5/2002 | Picard-Lesboucyries et al. |
| 2002/0164294 | A1 | | 11/2002 | Christophides-Lordi et al. |
| 2002/0165508 | A1 | | 11/2002 | Klofta et al. |
| 2002/0182158 | A1 | | 12/2002 | Christophides-Lordi et al. |
| 2002/0192169 | A1 | | 12/2002 | Chevalier et al. |
| 2002/0192245 | A1 | | 12/2002 | Jensen et al. |
| 2002/0192246 | A1 | | 12/2002 | Jensen et al. |
| 2003/0035824 | A1 | | 2/2003 | Isele et al. |
| 2003/0077307 | A1 | | 4/2003 | Klofta et al. |
| 2003/0078172 | A1 | | 4/2003 | Guiramand et al. |
| 2003/0082219 | A1 | | 5/2003 | Warren et al. |

FOREIGN PATENT DOCUMENTS

| | | |
|---|---|---|
| EP | 0 093 186 A1 | 11/1983 |
| EP | 0 682 868 A1 | 11/1995 |
| FR | 2614788 B1 | 11/1988 |
| FR | 2675341 A | 10/1992 |
| GB | 2216793 B | 10/1989 |
| WO | WO 99/45973 A1 | 9/1999 |
| WO | WO 99/45974 A1 | 9/1999 |
| WO | WO 99/62459 A2 | 12/1999 |
| WO | WO 00/74643 A1 | 12/2000 |
| WO | WO 01/17565 A2 | 3/2001 |
| WO | WO 01/43717 A1 | 6/2001 |

OTHER PUBLICATIONS

CAS Registry 41672-81-5.*
Ege, S. "Organic Chemistry" 1994, pp. 59, 586, and 1205.*
pKa Data Compiled by R. Williams, downloaded from the world wide web on Sept. 12, 2006.*

* cited by examiner

*Primary Examiner*—Michael P. Woodward
*Assistant Examiner*—Eric E. Silverman
(74) *Attorney, Agent, or Firm*—Eric T. Addington; John H. Howell; Brian M. Bolam

(57) ABSTRACT

Skin care compositions and methods for regulating the condition of mammalian keratinous tissue containg an effective amount of a dialkanoyl hydroxyproline compound and a second skin care compound selected from hexamidine compounds, sugar amine compounds and their combination. These compositions may be either an emulsion or a solution wherin the dialkanoyl hydroxyproline compound may be converted to its salt for incorporation into the aqueous phase of a compositions.

21 Claims, No Drawings

COMPOSITIONS AND METHODS FOR REGULATING MAMMALIAN KERATINOUS TISSUE

TECHNICAL FIELD

The present invention relates to topical compositions containing a combination of dialkanoyl hydroxyproline compounds and their salts and derivatives in combination with hexamidine compounds and their salts and derivatives and/or sugar amine compounds and their salts and derivatives. Such compositions are useful for regulating the condition of mammalian keratinous tissue using defined dialkanoyl hydroxyproline compounds along with at least one additional skin care active selected from hexamidine compounds and sugar amine compounds. Also disclosed are methods, as outlined below, for such regulation of keratinous tissue. These cosmetic methods are accomplished via the topical application, to the skin of a mammal needing such treatments, compositions containing a) a dialkanoyl hydroxyproline compound and at least one additional skin care active selected from hexamidine compounds and sugar amine compounds or b) neutralized dialkanoyl hydroxy proline salts incorporated into the aqueous phase of either an emulsion or a solution.

BACKGROUND OF THE INVENTION

Currently, there are a number of personal care products that are available to consumers, which are directed toward improving the physical appearance and health of keratinous tissues such as the skin, hair, and nails. The majority of these products are directed to delaying, minimizing or even eliminating skin wrinkling and other histological changes typically associated with the aging of skin or environmental damage to human skin. Numerous compounds have been described in the art as being useful for regulating skin condition, including regulating fine lines, wrinkles, skin texture, sagging and skin discoloration.

Mammalian keratinous tissue, particularly human skin, is subjected to a variety of insults by both extrinsic and intrinsic factors. Such extrinsic factors include ultraviolet radiation, environmental pollution, wind, heat, infrared radiation, low humidity, harsh surfactants, abrasives, etc. Intrinsic factors, on the other hand, include chronological aging and other biochemical changes from within the skin. Whether extrinsic or intrinsic, these factors result in visible signs of skin damage. Typical skin damage includes thinning of the skin, which occurs naturally as one ages. With such thinning, there is a reduction in the cells and blood vessels that supply the skin as well as a flattening of the dermal-epidermal junction that results in weaker mechanical resistance of this junction. See, for example, Oikarinen, "The Aging of Skin: Chronoaging Versus Photoaging," *Photodermatol. Photoimmunol. Photomed.*, vol. 7, pp. 3-4, 1990. Other damages or changes seen in aging or damaged skin include fine lines, wrinkling, hyperpigmentation, sallowness, sagging, dark under-eye circles, puffy eyes, enlarged pores, diminished rate of turnover, and abnormal desquamation or exfoliation. Additional damage incurred as a result of both external and internal factors includes visible dead skin (i.e., flaking, scaling, dryness, roughness).

Therefore, there is a need for products and methods that seek to remedy these keratinous tissue conditions. A large number of skin care actives are known in the art and used to improve the physical appearance and/or health of the skin. For example, salicylic acid and benzoyl peroxide are used in skin care compositions to treat acne. Retinoids are another example of skin care actives used in skin care compositions to reduce signs of aging skin. Although formulating skin care compositions with such actives provide skin care benefits, there are also challenges in formulating such compositions. For example, retinoid compositions typically have to be prepared under specialized conditions, such as inert atmosphere, and may exhibit less than optimal stability, such as discoloration, at times. Some skin care actives may result in skin irritation, such as stinging, burning and redness.

Based on the foregoing, there is a continuing need to formulate skin care compositions which improve the physical appearance and/or health of the skin, which are for example, aesthetically pleasing, stable and effective at treating the appearance of wrinkles, fine lines, pores, poor skin color (redness, sallowness and other forms of undesirable skin surface texture).

Surprisingly, it has now been found that compositions containing dialkanoyl hydroxyprolines compounds, their salts and derivatives thereof when in combination with hexamidine compounds, its salts and derivatives thereof and/or sugar amine compounds, its salts and derivatives thereof provide benefits in regulating skin condition previously unrecognized in the art of which the inventors are aware. For example, topical application of dipalmitoyl hydroxyproline and hexamidine and/or N-acetyl glucosamine is believed to synergistically regulate (prophylactically and/or therapeutically) visible and or tactile discontinuities in mammalian skin. Additionally surprising is the fact that neutralized salts of dialkanoyl hydroxyprolines can be incorporated into the aqueous phase of a composition, such as a solution or an emulsion resulting in improved stability of these compositions.

For instance, Applicants have found that such compositions may be useful for preventing, retarding, and/or treating dark under-eye circles, puffy eyes, sagging, sallowness as well as spider vessels and/or red blotchiness of skin, promoting skin desquamation, exfoliation, and/or turnover, regulating and/or reducing pore size appearance, preventing/retarding tanning, regulating oily/shiny appearance, preventing, retarding, and/or treating hyperpigmentation (such as post-inflammatory hyperpigmentation, pigment spots such as age spots, and the like) in mammalian skin, preventing, retarding, and/or treating itchiness of mammalian skin, preventing, retarding, and/or treating dryness of skin, preventing, retarding, and/or treating fine lines and wrinkles, preventing, retarding, and/or treating skin atrophy of mammalian skin, softening and/or smoothing lips, hair and nails of a mammal, and preventing, retarding, and/or treating the appearance of cellulite in mammalian skin.

SUMMARY OF THE INVENTION

The present invention relates both to the compositions and to methods for regulating the condition of mammalian keratinous tissue wherein the methods each comprise the step of topically applying to the keratinous tissue of a mammal needing such treatment, a safe and effective amount of a skin care composition comprising:
  a) a safe and effective amount of a dialkanoyl hydroxyproline compound selected from the group consisting of dialkanoyl hydroxyproline, its salts, and derivatives;
  b) a safe and effective amount of a skin care active selected from the group consisting of hexamidine compounds and salts and derivatives thereof, sugar amine compounds and their salts and derivatives thereof, and mixtures thereof; and
  c) a dermatologically acceptable carrier.

Preferably, the weight ratio of the dialkanoyl hydroxyproline compound to the hexamidine compound, the sugar amine compound or combinations thereof is from 1:12 to 1:0.1.

In an additional embodiment the present invention relates to compositions and to methods for regulating the condition of mammalian keratinous tissue wherein the methods each comprise the step of topically applying to the keratinous tissue of a mammal needing such treatment, a safe and effective amount of a skin care composition comprising:
  a) a safe and effective amount of dialkanoyl hydroxyproline salts wherein the salt is incorporated into the aqueous phase of a composition; and
  b) a dermatologically acceptable carrier for the composition. The composition can be either a water containing emulsion or an aqueous solution or dispersion.

Upon making oil-in-water emulsions of the present invention, many such emulsions will not have sufficient oil present to adequately solubilize the oil-soluble dialkanoyl hydroxyproline compound that's not in a water-soluble salt form. To facilitate manufacturing such emulsion compositions, it has been found that a process including the initial formation of a dialkanoyl hydroxyproline salt simplifies the manufacturing method of making such emulsions.

DETAILED DESCRIPTION OF THE INVENTION

All percentages and ratios used herein are by weight of the total composition and all measurements made are at 25° C., unless otherwise designated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

All documents cited are, in relevant part, incorporated herein by reference; the citation of any document is not to be construed as an admission that it is prior art with respect to the present invention.

The term "keratinous tissue," as used herein, refers to keratin-containing layers disposed as the outermost protective covering of mammals which includes, but is not limited to, skin, hair, toenails, fingernails, cuticles, hooves, etc.

The term "topical application", as used herein, means to apply or spread the compositions of the present invention onto the surface of the keratinous tissue.

The term "dermatologically acceptable," as used herein, means that the compositions or components thereof so described are suitable for use in contact with human keratinous tissue without undue toxicity, incompatibility, instability, allergic response, and the like.

The term "safe and effective amount" as used herein means an amount of a compound or composition sufficient to significantly induce a positive benefit, preferably a positive keratinous tissue appearance or feel benefit, including independently or in combinations the benefits disclosed herein, but low enough to avoid serious side effects, i.e., to provide a reasonable benefit to risk ratio, within the scope of sound judgment of the skilled artisan.

The term "post-inflammatory hyperpigmentation" as used herein refers to the changes in melanin content as a response to an inflammatory event (e.g., acne, scratch, insect sting, sunburn, etc), especially in dark skin subjects.

The term "derivatives" as used herein refers to structures which are not shown but which one skilled in the art would understand are variations of the basic compound. For example, removing a hydrogen atom from benzene and replacing it with a methyl group.

The term "hyperpigmentation" as used herein refers to an area of skin wherein the pigmentation is greater than that of an adjacent area of skin (e.g., a pigment spot, an age spot, and the like).

The terms "desquamation, exfoliation, and/or increasing turnover" as used herein mean the removal of the upper layers of the stratum corneum (comprising the horny layers). Without intending to be limited by theory, it is believed that these benefits may be accomplished via chemical and physical means that remove these layers from the top down. Additionally, it is possible to elicit exfoliation via a biological means that drives the turnover of the epidermal layers from the viable layers (e.g., basal layers) upwards. It is believed that this involves the process of keratinocyte proliferation and/or as induction of differentiation. The latter leads to an elevation in keratinization levels as well, which ultimately leads to a reorganization of the upper epidermal layers that comprise the spinous and stratum granulosum layers.

The terms "oily and/or shiny appearance" as used herein mean the glossy look mammalian skin tends to exhibit upon the excretion of oil, sebum, and/or sweat from the respective source gland.

The term "sagging" as used herein means the laxity, slackness, or the like condition of skin that occurs as a result of loss of, damage to, alterations to, and/or abnormalities in dermal elastin.

The term "smoothing" and "softening" as used herein means altering the surface of the keratinous tissue such that its tactile feel is improved.

The term "sallowness" as used herein means the pale color, yellow color or the like condition of skin that occurs as a result of a loss of, damage to, alterations to, and/or abnormalities in skin components such that they become colored (e.g., yellow in color) due to processes such as protein glycation and accumulation of lipofuscin or in the decrease in peripheral blood flow that typically accompanies skin aging.

The compositions of the present invention are useful for topical application and for regulating keratinous tissue condition. Regulation of keratinous tissue condition, especially human skin condition, is often required due to conditions that may be induced or caused by factors internal and/or external to the body. For instance, "regulating skin condition" includes prophylactically regulating and/or therapeutically regulating skin condition, and may involve one or more of the following benefits: thickening (i.e., building the epidermis and/or dermis layers of the skin and/or the subcutaneous layers such as fat and muscle and where applicable the keratinous layers of the nail and hair shaft) to reduce atrophy (e.g., of the skin), increasing the convolution of the dermal-epidermal border, non-melanin skin discoloration such as under eye circles, blotching (e.g., uneven red coloration due to, e.g., rosacea) (hereinafter referred to as "red blotchiness"), sallowness (pale or yellow color), discoloration caused by telangiectasia or spider vessels, discolorations due to melanin (e.g., pigment spots, age spots, uneven pigmentation) and other chromophores in the skin (e.g., lipofuscin, protein crosslinks such as those that occur with glycation, and the like). As used herein, prophylactically regulating skin condition includes delaying, minimizing and/or preventing visible and/or tactile discontinuities in skin (e.g., texture irregularities, fine lines, wrinkles, sagging, stretch marks, cellulite, puffy eyes, and the like in the skin which may be detected visually or by feel). As used herein, therapeutically regulating skin condition includes ameliorating, e.g., diminishing, minimizing and/or effacing, discontinuities in skin. Regulating skin condition involves improving skin appearance and/or feel.

As used herein, "regulating skin condition" is intended to include regulation of such signs irrespective of the mechanism of origin.

The compositions of the present invention, including the essential and optional components thereof, are described in detail hereinafter.

I. The Compositions

A. Dialkanoyl Hydroxyproline Compounds

The topical compositions of the present invention comprise a safe and effective amount of one or more dialkanoyl hydroxyproline compounds and their salts and derivatives. In the composition of the present invention, the dipalmitoyl hydroxyproline compounds preferably comprise from about 0.01 to 10%, more preferably from about 0.1-5%, more and most preferably from about 0.1 to 2% by weight of the composition Suitable derivatives include but are not limited to esters, for example fatty esters, including, but not limited to tripalmitoyl hydroxyproline and dipalmityl acetyl hydroxyproline. A particularly useful compound is dipalmitoyl hydroxyproline. As used herein, dipalnutoyl hydroxyproline" includes any isomers and tautomers of such and is commercially available under the tradename Sepilift DPHP® from Seppic, Inc. Further discussion of dipalmitoyl hydroxy proline appears in PCT Publication WO 93/23028. Preferably the dipalmitoyl hydroxyproline is the triethanolamine salt of dipalmitoyl hydroxyproline.

B. Skin Care Actives (Hexamidine and Sugar Amine Compounds)

The composition of the present invention includes use of an additional skin care active with dialkanoyl hydroxyproline compounds disclosed above. This additional skin care active is selected from the group consisting of hexamidine compounds, its salts and its derivatives, sugar amine compounds, its salts and derivatives and mixtures thereof. Preferably, the weight ratio of the dialkanoyl hydroxyproline compound, the sugar amine compound or combinations thereof is 1:12 to 1.0 to 0.1.

Hexamidine Compounds

The hexamidine compounds useful in the present invention correspond to those of the following chemical structure:

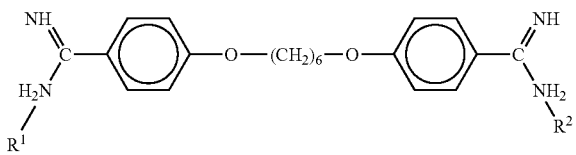

wherein $R^1$ and $R^2$ comprise organic acids (e.g., sulfonic acids, etc.).

In the composition of the present invention, the hexamidine compound preferably comprises from about, 0.001-10%, more preferably from about 0.01-5%, and most preferably from about 0.02-2.5%.

The topical compositions of the present invention optionally include a safe and effective amount of one or more of hexamidine compounds, its salts and its derivatives. As used herein, hexamidine derivatives includes any isomers and tautomers of hexamidine compounds including but not limited to organic acids and mineral acids, for example sulfonic acid, carboxylic acid etc. Preferably, the hexamidine compounds include hexamidine diisethionate, commercially available as Elestab® HP100 from Laboratoires Serobiologiques (Pulnoy, France).

Sugar Amine Compounds (Amino Sugars)

The compositions of the present invention optionally include a safe and effective amount of a sugar amine, which are also known as amino sugars. The sugar amine compounds useful in the present invention are described in PCT Publication WO 02/076423, published Oct. 3, 2000 and U.S. Pat. No. 6,159,485, issued Dec. 12, 2000.

Preferably, the composition contains from about 0.01% to about 15%, more preferably from about 0.1% to about 10%, and most preferably from about 0.5% to about 5% by weight of the composition, of the sugar amine.

Sugar amines can be synthetic or natural in origin and can be used as essentially as pure compounds or mixtures of compounds (e.g., extracts from natural sources or mixtures of synthetic materials). Glucosamine is generally found in many shellfish and can also be derived from fungal sources. As used herein, "sugar amine" includes isomers and tautomers of such and its salts (e.g., HCl salt) and its derivatives and is commercially available from Sigma Chemical Co., St. Louis, Mo.

Examples of sugar amines that are useful herein include glucosamine, N-acetyl glucosamine, mannosamine, N-acetyl mannosamine, galactosamine, N-acetyl galactosamine, their isomers (e.g., stereoisomers), and their salts (e.g., HCl salt). Preferred for use herein are glucosamine, particularly D-glucosamine and N-acetyl glucosamine, particularly N-acetyl-D-glucosamine. Additionally, combinations of two or more sugar amines may be used. The topical compositions of the present invention also comprise a safe and effective amount of one or more glucosamine compounds. Most preferred for use herein is N-acetyl D-glucosamine.

C. Dermatologically Acceptable Carrier

The topical compositions of the present invention also comprise a dermatologically acceptable carrier for the disclosed compositions. The phrase "dermatologically acceptable carrier", as used herein, means that the carrier is suitable for topical application to the keratinous tissue, has good aesthetic properties, is compatible with the actives of the present invention and any other components, and will not cause any safety or toxicity concerns. A safe and effective amount of carrier is from about 50% to about 99.99%, preferably from about 60% to about 99.9%, and most preferably from about 70% to about 98% of the composition.

The carrier can be in a wide variety of types. For example, emulsion carriers, including, but not limited to, oil-in-water, water-in-oil, water-in-oil-in-water, and oil-in-water-in-oil emulsions, are useful herein. In these emulsion carriers, silicone can also be used as the oil, thus yielding silicone-in-water, water-in-silicone, water-in-silicone-in-water and oil-in-water-in-silicone emulsions. In addition, water or water based carriers are an acceptable carrier for those embodiments comprising dialkanoyl hydroxyproline salts, while oils or oil-based carriers are acceptable carriers for non-salt forms of dialkanoyl hydroxyproline. These carriers can also take many forms, non-limiting examples of which include liquids, milks, serums, lotions, creams, sprays, aerosols, mousses, foams, sticks, gels, and pencils.

Preferred carriers comprise an emulsion such as oil-in-water emulsions, including silicone in-water and water-in-oil emulsions, including water-in-silicone emulsions. As will be understood by the skilled artisan, a given component will distribute primarily into either the water or oil phase, depending on the water solubility/dispensability of the component in the composition. Oil-in-water emulsions are especially preferred, and silicone-in-water emulsions are even more preferred.

Emulsions according to the present invention generally contain an aqueous solution described above and a lipid or oil. Lipids and oils may be derived from animals, plants, or petroleum and may be natural or synthetic (i.e., man-made, such as silicones). Preferred emulsions also contain a humectant, such as glycerin. Emulsions will preferably further contain from about 0.05% to about 10%, more preferably from about 0.1% to about 5%, of an emulsifier, based on the weight of the composition. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and *McCutcheon's Detergents and Emulsifiers*, North American Edition, pages 317-324 (1986).

Suitable emulsions may have a wide range of viscosities, depending on the desired product form.

Preferred water-in-oil and oil-in-water emulsions are described in greater detail below.

1) Water-in-Oil Emulsion

Water in oil emulsions are characterized as having a continuous hydrophobic, water insoluble oil phase and a water phase dispersed therein. The "oil phase" can contain oil, silicone or mixtures thereof. The distinction of whether the emulsion is characterized as a water-in-oil or water-in-silicone emulsion is a function of whether the oil phase is composed of primarily oil or silicone. A preferred example of a water-in-silicone emulsion is described below.

A. Continuous Silicone Phase

Preferred water-in-silicone emulsions of the present invention comprise from about 1% to about 60%, preferably from about 5% to about 40%, more preferably from about 10% to about 30%, by weight of a continuous silicone phase. The continuous silicone phase exists as an external phase that contains or surrounds the discontinuous aqueous phase described hereinafter.

The continuous silicone phase contains an silicone elastomer and or polyorganosiloxane oil. The continuous silicone phase of these preferred emulsions comprises between about 50% and about 99.9% by weight of organopolysiloxane oil and less than about 50% by weight of a non-silicone oil. In a preferred embodiment, the continuous silicone phase comprises at least about 50%, preferably from about 60% to about 99.9%, more preferably from about 70% to about 99.9%, and even more preferably from about 80% to about 99.9%, polyorganosiloxane oil by weight of the continuous silicone phase, and up to about 50% non-silicone oils, preferably less about 40%, more preferably less than about 30%, even more preferably less than about 10%, and most preferably less than about 2%, by weight of the continuous silicone phase.

1) Polyorganopolysiloxane Oil

The organopolysiloxane oil for use in the composition may be volatile, non-volatile, or a mixture of volatile and non-volatile silicones. The term "nonvolatile" as used in this context refers to those silicones that are liquid under ambient conditions and have a flash point (under one atmospheric of pressure) of or greater than about 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Polyalkylsiloxanes useful in the composition herein include polyalkylsiloxanes with viscosities of from about 0.5 to about 1,000,000 centistokes at 25° C. Such polyalkylsiloxanes can be represented by the general chemical formula $R_3SiO[R_2SiO]_xSiR_3$ wherein R is an alkyl group having from one to about 30 carbon atoms (preferably R is methyl or ethyl, more preferably methyl; also mixed alkyl groups can be used in the same molecule), and x is an integer from 0 to about 10,000, chosen to achieve the desired molecular weight which can range to over about 10,000,000. Commercially available polyalkylsiloxanes include the polydimethylsiloxanes, which are also known as dimethicones, examples of which include the Vicasil® series sold by General Electric Company and the Dow Corning® 200 series sold by Dow Corning Corporation. Specific examples of suitable polydimethylsiloxanes include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Suitable dimethicones include those represented by the chemical formula $(CH_3)_3SiO[(CH_3)_2SiO]_x[CH_3RSiO]_ySi(CH_3)_3$ wherein R is straight or branched chain alkyl having from two to about 30 carbon atoms and x and y are each integers of 1 or greater selected to achieve the desired molecular weight which can range to over about 10,000,000. Examples of these alkyl-substituted dimethicones include cetyl dimethicone and lauryl dimethicone.

Cyclic polyalkylsiloxanes suitable for use in the composition include those represented by the chemical formula $[SiR_2-O]_n$ wherein R is an alkyl group (preferably R is methyl or ethyl, more preferably methyl) and n is an integer from about 3 to about 8, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6).

Also useful are materials such as trimethylsiloxysilicate, which is a polymeric material corresponding to the general chemical formula $[(CH_3)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid.

Dimethiconols are also suitable for use in the composition. These compounds can be represented by the chemical formulas R₃SiO[R₂SiO]$_x$SiR₂OH and HOR₂SiO[R₂SiO]$_x$SiR₂OH wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids).

Polyalkylaryl siloxanes are also suitable for use in the composition. Polymethylphenyl siloxanes having viscosities from about 15 to about 65 centistokes at 25° C. are especially useful.

Preferred for use herein are organopolysiloxanes selected from the group consisting of polyalkylsiloxanes, alkyl substituted dimethicones, cyclomethicones, trimethylsiloxysilicates, dimethiconols, polyalkylaryl siloxanes, and mixtures thereof. More preferred for use herein are polyalkylsiloxanes and cyclomethicones. Preferred among the polyalkylsiloxanes are dimethicones.

As stated above, the continuous silicone phase may contain one or more non-silicone oils. Suitable non-silicone oils have a melting point of about 25° C. or less under about one atmosphere of pressure. Examples of non-silicone oils suitable for use in the continuous silicone phase are those well known in the chemical arts in topical personal care products in the form of water-in-oil emulsions, e.g., mineral oil, vegetable oils, synthetic oils, semisynthetic oils, etc.

2) Silicone Elastomer

The compositions of the present invention also include from about 0.1% to about 30%, by weight of the composition, of a silicone elastomer component. Preferably, the composition includes from about 1% to about 20%, more preferably from about 2% to about 10%, by weight of the composition, of the silicone elastomer component.

Suitable for use herein are silicone elastomers, which can be emulsifying or non-emulsifying crosslinked siloxane elastomers or mixtures thereof. No specific restriction exists as to the type of curable organopolysiloxane composition which can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane; condensation-curing organopolysiloxane compositions which cure in the presence of an organotin compound or a titanate ester, by a condensation reaction between an hydroxyl-terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation, or electron beams.

Addition reaction-curing organopolysiloxane compositions are preferred for their rapid curing rates and excellent uniformity of curing. A particularly preferred addition reaction-curing organopolysiloxane composition is prepared from:

(A) an organopolysiloxane having at least 2 lower alkenyl groups in each molecule;
(B) an organopolysiloxane having at least 2 silicon-bonded hydrogen atoms in each molecule; and
(C) a platinum-type catalyst.

With regard to the above, component (A) is the basic component of the silicone elastomer-generating organopolysiloxane, and curing proceeds by the addition reaction of this component with component (B) under catalysis by component (C). This component (A) must contain at least 2 silicon-bonded lower alkenyl groups in each molecule; an excellent cured product will not be obtained at few than two lower alkenyl groups because a network structure will not be formed. Said lower alkenyl groups are exemplified by vinyl, allyl, and propenyl. While the lower alkenyl groups can be present at any position in the molecular, their presence at the molecular terminals is preferred. The molecular structure of this component may be straight chain, branched straight chain, cyclic, or network, but a straight chain, possibly slightly branched, is preferred. The molecular weight of the component is not specifically restricted, and thus the viscosity may range from low viscosity liquids to very high viscosity gums. In order for the cured product to be obtained in the form of the rubbery elastomer, it is preferred that the viscosity at 25 degrees Centigrade be at least 100 centistokes. These organopolysiloxanes are exemplified by methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl) polysiloxanes, and dimethylvinylsiloxy-terminated dimethylsiloxane-methyl(3,3,-trifluoropropyl)siloxane copolymers.

Component (B) is an organopolysiloxane having at least 2 silicon-bonded hydrogen atoms in each molecule and is a crosslinker for component (A). Curing proceeds by the addition reaction of the silicon-bonded hydrogen atoms in this component with the lower alkenyl groups in component (A) under catalysis by component (C). This component (B) must contain at least 2 silicon-bonded hydrogen atoms in each molecule in order to function as a crosslinker. Furthermore, the sum of the number of alkenyl groups in each molecule of component (A) and the number of silicon-bonded hydrogen atoms in each molecule of component (B) is to be at least 5. Values below 5 should be avoided because a network structure is then essentially not formed.

No specific restriction exists on the molecular structure of this component, and it may be any of straight chain, branch-containing straight chain, cyclic, etc. The molecular weight of this component is not specifically restricted, but it is preferred that the viscosity at 25 degrees Centigrade be 1 to 50,000 centistokes in order to obtain good miscibility with component (A). It is preferred that this component be added in a quantity such that the molar ratio between the total quantity of silicon-bonded hydrogen atoms in the instant component and the total quantity of all lower alkenyl groups in component (A) falls within the range of (1.5:1) to (20:1). It is difficult to obtain good curing properties when this molar ratio falls below 0.5:1. When (20:1) is exceeded, there is a tendency for the hardness to increase to high levels when the cured product is heated. Furthermore, when an organosiloxane containing substantial alkenyl is supplementarily added for the purpose of; for example, reinforcement, it is preferred that a supplemental addition of the instant SiH-containing component be made in a quantity offsetting these alkenyl groups. This component is concretely exemplified by trimethylsiloxy-terminated methylhydrogenpolysiloxanes, trimethylsiloxy-terminated dimethylsiloxane-methylhydrogensiloxane copolymers, and dimethylsiloxane-methylhydrogen-siloxane cyclic copolymers.

Component (C) is a catalyst of the addition reaction of silicon-bonded hydrogen atoms and alkenyl groups, and is concretely exemplified by chloroplatinic acid, possibly dissolved in an alcohol or ketone and this solution optionally aged, chloroplatinic acid-olefin complexes, chloroplatinic acid-alkenylsiloxane complexes, chloroplatinic acid-diketone complexes, platinum black, and carrier-supported platinum.

Component C is added preferably at 0.1 to 1,000 weight parts, and more preferably at 1 to 100 weight parts, as platinum-type metal proper per 1,000,000 weight parts of the total quantity of components (A) plus (B). Other organic groups which may be bonded to silicon in the organopolysiloxane forming the basis for the above-described curable organopolysiloxane compositions are, for example, alkyl groups such as methyl, ethyl, propyl, butyl, and octyl; substituted alkyl groups such as 2-phenylethyl, 2-phenylpropyl, and 3,3,3-trifluoropropyl; aryl groups such as phenyl, tolyl, and xylyl; substituted aryl groups such as phenylethyl; and monovalent hydrocarbon groups substituted by, for example, the epoxy group, the carboxylate ester group, the mercapto group, etc.

Examples of the production of the organopolysiloxane elastomer powder are as follows: an organopolysiloxane composition as described above (additional-curable, condensation-curable, or peroxide-curable) is mixed with water in the presence of a surfactant (nonionic, anionic, cationic, or amphoteric), and, after mixing to homogeneity in a homomixer, colloid mill, homogenizer, propeller mixer, etc., this is cured by discharge into hot water (temperature at least 50 degrees Centigrade) and is then dried; the organopolysiloxane composition (addition-curable, condensation-curable, or peroxide-curable) is cured by spraying it directly into a heated current; the powder is obtained by curing a radiation-curable organopolysiloxane composition by spraying it under high energy radiation; the organopolysiloxane composition (addition-curable, condensation-curable, peroxide-curable) or high energy-curable organopolysiloxane composition is cured, the latter by high energy radiation, and the product is then pulverized using a known pulverizer such as, for example, a ball mill, atomizer, kneader, roll mill, etc., to thereby form the powder.

The compositions of the present invention may include an emulsifying crosslinked organopolysiloxane elastomer, a non-emulsifying crosslinked organopolysiloxane elastomer, or a mixture thereof. The term "non-emulsifying," as used herein, defines crosslinked organopolysiloxane elastomers from which polyoxyalkylene units are absent. The term "emulsifying," as used herein, means crosslinked organopolysiloxane elastomers having at least one polyoxyalkylene (e.g., polyoxyethylene or polyoxypropylene) unit. Preferred emulsifying elastomers herein include polyoxyalkylene modified elastomers formed from divinyl compounds, particularly siloxane polymers with at least two free vinyl groups, reacting with Si—H linkages on a polysiloxane backbone. Preferably, the elastomers are dimethyl polysiloxanes crosslinked by Si—H sites on a molecularly spherical MQ resin. Emulsifying crosslinked organopolysiloxane elastomer can notably be chosen from the crosslinked polymers described in U.S. Pat. No. 5,412,004 (issued May 12, 1995); U.S. Pat. No. 5,837,793 (issued Nov. 17, 1998); and U.S. Pat. No. 5,811,487 (issued Sep. 22, 1998), all of which are herein incorporated by reference in their entirety. In addition, an emulsifying elastomer comprised of dimethicone copolyol crosspolymer (and) dimethicone is available from Shin Etsu under the tradename KSG-21.

The silicone elastomers of the present invention may be further processed by subjecting them to a high shear (approximately 5,000 psi) treatment in the presence of a solvent for the silicone elastomer via a Sonolator with or without recycling in from 1 to 60 passes in order to result in a particular average particle size of silicone elastomer. Less than 10 passes results in an average particle size ranging from about 20 to 200 microns. From 10 to 60 passes results in an average particle size of less than 20 microns as measured by the Horiba LA-910. As used herein, the term "particle size" of the elastomer represents the elastomer particle size in its swelled state. By "swelled," as used herein, means the that the elastomer particles have extended beyond their normal size and shape by virtue of their absorption of the solvent compound.

Advantageously, the non-emulsifying elastomers are dimethicone/vinyl dimethicone crosspolymers. Such dimethicone/vinyl dimethicone crosspolymers are supplied by a variety of suppliers including Dow Corning (DC 9040 and DC 9041), General Electric (SFE 839), Shin Etsu (KSG-15, 16, 18 [dimethicone/phenyl vinyl dimethicone crosspolymer]), and Grant Industries (GRANSIL™ line of elastomers). Cross-linked organopolysiloxane elastomers useful in the present invention and processes for making them are further described in U.S. Pat. No. 4,970,252 to Sakuta, et al., issued Nov. 13, 1990; U.S. Pat. No. 5,760,116 to Kilgour, et al., issued Jun. 2, 1998; U.S. Pat. No. 5,654,362 to Schulz, Jr., et al. issued Aug. 5, 1997, all of which are herein incorporated by reference. Additional crosslinked organopolysiloxane elastomers useful in the present invention are disclosed in Japanese Patent Application JP 61-18708, assigned to Pola Kasei Kogyo KK.

Commercially available elastomers preferred for use herein are Dow Corning's 9040 silicone elastomer blend, Shin Etsu's KSG-21, and mixtures thereof 3) Carrier for Silicone Elastomer The topical compositions of the present invention include from about 1% to about 80%, by weight of the composition, of a suitable carrier for the for the crosslinked organopolysiloxane elastomer component described above. The carrier, when combined with the cross-linked organopolysiloxane elastomer particles of the present invention, serves to suspend and swell the elastomer particles to provide an elastic, gel-like network or matrix. The carrier for the cross-linked siloxane elastomer is liquid under ambient conditions, and preferably has a low viscosity to provide for improved spreading on the skin.

Concentrations of the carrier in the cosmetic compositions of the present invention will vary primarily with the type and amount of carrier and the cross-linked siloxane elastomer employed. Preferred concentrations of the carrier are from about 5% to about 50%, more preferably from about 5% to about 40%, by weight of the composition.

The carrier for the cross-linked siloxane elastomer includes one or more liquid carriers suitable for topical application to human skin. These liquid carriers may be organic, silicone-containing or fluorine-containing, volatile or non-volatile, polar or non-polar, provided that the liquid carrier forms a solution or other homogenous liquid or liquid dispersion with the selected cross-linked siloxane elastomer at the selected siloxane elastomer concentration at a temperature of from about 28° C. to about 250° C., preferably from about 28° C. to about 100° C., preferably from about 28° C. to about 78° C. The carrier for the cross-linked siloxane elastomer preferably has a solubility parameter of from about 3 to about 13 $(cal/cm^3)^{0.5}$, more preferably from about 5 to about 11 $(cal/cm^3)^{0.5}$, most preferably from about 5 to about 9 $(cal/cm^3)^{0.5}$. Solubility parameters for the liquid carriers or other materials, and means for determining such parameters, are well known in the chemical arts. A description of solubility parameters and means for determining them are described by C. D. Vaughan, "Solubility Effects in Product, Package, Penetration and Preservation" 103 Cosmetics and Toiletries 47-69, October 1988; and C. D. Vaughan, "Using Solubility Parameters in Cosmetics Formulation", 36 J. Soc. Cosmetic Chemists 319-333, September/October, 1988, which articles are incorporated herein by reference.

The carrier preferably includes volatile, non-polar oils; non-volatile, relatively polar oils; non-volatile, non-polar oils; and non-volatile paraffinic hydrocarbon oils; each discussed more fully hereinafter. The term "non-volatile" as used herein refers to materials which exhibit a vapor pressure of no more than about 0.2 mm Hg at 25° C. at one atmosphere and/or to materials which have a boiling point at one atmosphere of at least about 300° C. The term "volatile" as used herein refers to all materials which are not "non-volatile" as previously defined herein. The phrase "relatively polar" as used herein means more polar than another material in terms of solubility parameter; i.e., the higher the solubility parameter the more polar the liquid. The term "non-polar" typically means that the material has a solubility parameter below about 6.5 $(cal/cm^3)^{0.5}$.

1. Non-polar, Volatile Oils

The non-polar, volatile oil tends to impart highly desirable aesthetic properties to the compositions of the present invention. Consequently, the non-polar, volatile oils are preferably utilized at a fairly high level. Non-polar, volatile oils particularly useful in the present invention are silicone oils; hydrocarbons; and mixtures thereof. Such non-polar, volatile oils are disclosed, for example, in Cosmetics, Science, and Technology, Vol. 1, 27-104 edited by Balsam and Sagarin, 1972. The non-polar, volatile oils useful in the present invention may be either saturated or unsaturated, have an aliphatic character and be straight or branched chained or contain alicyclic or aromatic rings. Examples of preferred non-polar, volatile hydrocarbons include polydecanes such as isododecane and isodecane (e.g., Permethyl-99A which is available from Presperse Inc.) and the C7-C8 through C12-C15 isoparaffins (such as the Isopar Series available from Exxon Chemicals). Non-polar, volatile liquid silicone oils are disclosed in U.S. Pat. No. 4,781,917 issued to Luebbe et al. on Nov. 1, 1988, herein incorporated by reference in its entirety. Additionally, a description of various volatile silicones materials is found in Todd et al., "Volatile Silicone Fluids for Cosmetics", Cosmetics and Toiletries, 91:27-32 (1976), herein incorporated by reference in its entirety. Particularly preferred volatile silicone oils are selected from cyclic volatile silicones corresponding to the formula:

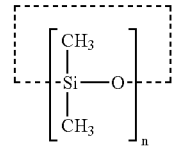

wherein n is from about 3 to about 7; and linear volatile silicones corresponding to the formula:

$(CH_3)_3Si-O-[Si(CH_3)_2-O]_m-Si(CH_3)_3$ wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.).

2. Relatively Polar, Non-Volatile Oils

The non-volatile oil is "relatively polar" as compared to the non-polar, volatile oil discussed above. Therefore, the non-volatile co-carrier is more polar (i.e., has a higher solubility parameter) than at least one of the non-polar, volatile oils. Relatively polar, non-volatile oils potentially useful in the present invention are disclosed, for example, in Cosmetics, Science, and Technology, Vol. 1, 27-104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989, all of which are herein incorporated by reference in their entirety. Relatively polar, non-volatile oils useful in the present invention are preferably selected from silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof. The relatively polar, non-volatile co-carriers useful in the present invention may be either saturated or unsaturated, have an aliphatic character and be straight or branched chained or contain alicyclic or aromatic rings. More preferably, the relatively polar, non-volatile liquid co-carrier is selected from fatty alcohols having from about 12-26 carbon atoms; fatty acids having from about 12-26 carbon atoms; esters of monobasic carboxylic acids and alcohols having from about 14-30 carbon atoms; esters of dibasic carboxylic acids and alcohols having from about 10-30 carbon atoms; esters of polyhydric alcohols and carboxylic acids having from about 5-26 carbon atoms; ethoxylated, propoxylated, and mixtures of ethoxylated and propoxylated ethers of fatty alcohols with from about 12-26 carbon atoms and a degree of ethoxylation and propoxylation of below about 50; and mixtures thereof. More preferred are propoxylated ethers of C14-C18 fatty alcohols having a degree of propoxylation below about 50, esters of C2-C8 alcohols and C12-C26 carboxylic acids (e.g. ethyl myristate, isopropyl palmitate), esters of C12-C26 alcohols and benzoic acid (e.g. Finsolv TN supplied by Finetex), diesters of $C_2$-$C_8$ alcohols and adipic, sebacic, and phthalic acids (e.g., diisopropyl sebacate, diisopropyl adipate, di-n-butyl phthalate), polyhydric alcohol esters of C6-C26 carboxylic acids (e.g., propylene glycol dicaprate/dicaprylate, propylene glycol isostearate); and mixtures thereof. Even more preferred are branched-chain aliphatic fatty alcohols having from about 12-26 carbon atoms. Even more preferred is isocetyl alcohol, octyldecanol, octyldodecanol and undecylpentadecanol; and most preferred is octyldodecanol. Such preferred aliphatic fatty alcohols are particularly useful in combination with the volatile liquid silicone oils discussed herein to adjust the average solubility of the carrier.

3. Non-Polar, Non-Volatile Oils

In addition to the liquids discussed above, the carrier for the cross-linked siloxane elastomer may optionally include non-volatile, non-polar oils. Typical non-volatile, non-polar emollients are disclosed, for example, in Cosmetics, Science, and Technology, Vol. 1, 27-104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989. Both of which are herein incorporated by reference. The non-volatile oils useful in the present invention are essentially non-volatile polysiloxanes, paraffinic hydrocarbon oils, and mixtures thereof. The polysiloxanes useful in the present invention selected from polyalkylsiloxanes, polyarylsiloxanes, polyalkylarylsiloxanes, polyethersiloxane copolymers, and mixtures thereof. Examples of these include polydimethyl siloxanes having viscosities of from about 1 to about 100,000 centistokes at 25° C. Among the preferred non-volatile silicone emollients useful in the present compositions are the polydimethyl siloxanes having viscosities from about 2 to about 400 centistokes at 25° C. Such polyalkylsiloxanes include the Viscasil series (sold by General Electric Company) and the Dow Corning 200 series (sold by Dow Corning Corp.). Polyalkylarylsiloxanes include polymethylphenyl siloxanes having viscosities of from about 15 to about 65 centistokes at 25° C. These are available, for example, as SF 1075 methyl-phenyl fluid (sold by General Electric Company) and 556 Cosmetic Grade Fluid (sold by Dow Corning Corp.). Useful polyethersiloxane copolymers include, for example, a polyoxyalkylene ether copolymer having a viscosity of about 1200 to 1500 centistokes at 25° C. Such a fluid is available as SF1066 organosilicone surfactant (sold by General Electric Company). Polysiloxane ethylene glycol ether copolymers are preferred copolymers for use in the present compositions.

Non-volatile paraffinic hydrocarbon oils useful in the present invention include mineral oils and certain branched-chain hydrocarbons. Examples of these fluids are disclosed in U.S. Pat. No. 5,019,375 issued to Tanner et al. on May 28, 1991, herein incorporated by reference in its entirety. Preferred mineral oils have the following properties:

(1) viscosity from about 5 centistokes to about 70 centistokes at 40° C.;

(2) density between about 0.82 and 0.89 g/cm3 at 25° C.;

(3) flash point between about 138° C. and about 216° C.; and (4) carbon chain length between about 14 and about 40 carbon atoms.

Preferred branched chain hydrocarbon oils have the following properties:

(1) density between about 0.79 and about 0.89 g/cm3 at 20° C.

(2) boiling point greater than about 250° C.; and (3) flash point between about 110° C. and about 200° C.

Particularly preferred branched-chain hydrocarbons include Permethyl 103 A, which contains an average of about 24 carbon atoms; Permethyl 104A, which contains an average of about 68 carbon atoms; Permethyl 102A, which contains an average of about 20 carbon atoms; all of which may be purchased from Permethyl Corporation; and Ethylflo 364 which contains a mixture of 30 carbon atoms and 40 carbon atoms and may be purchased from Ethyl Corp.

Additional carriers useful herein include solvents described in U.S. Pat. No. 5,750,096 to Gerald J. Guskey et al., issued May 12, 1998, herein incorporated by reference in its entirety.

(B) Dispersed Aqueous Phase

The topical compositions of the present invention comprise from about 30% to about 90%, more preferably from about 50% to about 85%, and most preferably from about 70% to about 80% of a dispersed aqueous phase. In emulsion technology, the term "dispersed phase" is a term well-known to one skilled in the art which means that the phase exists as small particles or droplets that are suspended in and surrounded by a continuous phase. The dispersed phase is also known as the internal or discontinuous phase. The dispersed aqueous phase is a dispersion of small aqueous particles or droplets suspended in and surrounded by the continuous silicone phase described hereinbefore.

The aqueous phase can be water, or a combination of water and one or more water soluble or dispersible ingredients. Nonlimiting examples of such optional ingredients include thickeners, acids, bases, salts, chelants, gums, water-soluble or dispersible alcohols and polyols, buffers, preservatives, sunscreening agents, colorings, and the like.

The topical compositions of the present invention will typically comprise from about 25% to about 90%, preferably from about 40% to about 80%, more preferably from about 60% to about 80%, water in the dispersed aqueous phase by weight of the composition.

(1) Emulsifier for Dispersing the Aqueous Phase

The water-in-silicone emulsions of the present invention preferably comprise an emulsifier. In a preferred embodiment, the composition contains from about 0.1% to about 10% emulsifier, more preferably from about 0.5% to about 7.5%, most preferably from about 1% to about 5%, emulsifier by weight of the composition. The emulsifier helps disperse and suspend the aqueous phase within the continuous silicone phase.

A wide variety of emulsifying agents can be employed herein to form the preferred water-in-silicone emulsion. Known or conventional emulsifying agents can be used in the composition, provided that the selected emulsifying agent is chemically and physically compatible with essential components of the composition, and provides the desired dispersion characteristics. Suitable emulsifiers include silicone emulsifiers, non-silicon-containing emulsifiers, and mixtures thereof, known by those skilled in the art for use in topical personal care products. Preferably these emulsifiers have an HLB value of or less than about 14, more preferably from about 2 to about 14, and most preferably from about 4 to about 14. Emulsifiers having an HLB value outside of these ranges can be used in combination with other emulsifiers to achieve an effective weighted average HLB for the combination that falls within these ranges.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethylsiloxanes that have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone copolyols, i.e., compounds that contain C2-C30 pendant side chains. Still other useful dimethicone copolyols include materials having various cationic, anionic, amphoteric, and zwitterionic pendant moieties.

The dimethicone copolyol emulsifiers useful herein can be described by the following general structure:

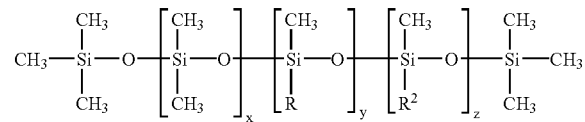

wherein R is C1-C30 straight, branched, or cyclic alkyl and $R^2$ is selected from the group consisting of:

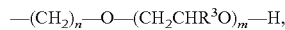

and

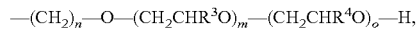

wherein n is an integer from 3 to about 10; $R^3$ and $R^4$ are selected from the group consisting of H and C1-C6 straight or branched chain alkyl such that $R^3$ and $R^4$ are not simultaneously the same; and m, o, x, and y are selected such that the molecule has an overall molecular weight from about 200 to about 10,000,000, with m, o, x, and y being independently selected from integers of zero or greater such that m and o are not both simultaneously zero, and z being independently selected from integers of 1 or greater. It is recognized that positional isomers of these copolyols can be achieved. The chemical representations depicted above for the $R^2$ moieties containing the $R^3$ and $R^4$ groups are not meant to be limiting but are shown as such for convenience.

Also useful herein, although not strictly classified as dimethicone copolyols, are silicone surfactants as depicted in the structures in the previous paragraph wherein $R^2$ is:

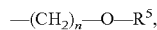

wherein $R^5$ is a cationic, anionic, amphoteric, or zwitterionic moiety.

Nonlimiting examples of dimethicone copolyols and other silicone surfactants useful as emulsifiers herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly(ethylene)(propylene)oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers containing pendant C2-C30 straight, branched, or cyclic alkyl moieties. Examples of commercially available dimethicone copolyols useful herein sold by Dow Corning Corporation are Dow Corning® 190, 193, Q2-5220, 2501 Wax, 2-5324 fluid, and 3225C (this latter material being sold as a mixture with cyclomethicone). Cetyl dimethicone copolyol is commercially available as a mixture with polyglyceryl-4 isostearate (and) hexyl laurate and is sold under the tradename ABIL® WE-09 (available from Goldschmidt). Cetyl dimethicone copolyol is also commercially available as a mixture with hexyl laurate (and) polyglyceryl-3 oleate (and) cetyl dimethicone and is sold under the tradename ABIL® WS-08 (also available from Goldschmidt). Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate. See *International Cosmetic Ingredient Dictionary*, Fifth Edition, 1993.

Dimethicone copolyol emulsifiers useful herein are described, for example, in U.S. Pat. No. 4,960,764, to Figueroa, Jr. et al., issued Oct. 2, 1990; European Patent No. EP 330,369, to Sanogueira, published Aug. 30, 1989; G. H. Dahms, et al., "New Formulation Possibilities Offered by Silicone Copolyols," *Cosmetics & Toiletries*, vol. 110, pp. 91-100, March 1995; M. E. Carlotti et al., "Optimization of W/O—S Emulsions And Study Of The Quantitative Relationships Between Ester Structure And Emulsion Properties," *J. Dispersion Science And Technology*, 13(3), 315-336 (1992); P. Hameyer, "Comparative Technological Investigations of Organic and Organosilicone Emulsifiers in Cosmetic Water-in-Oil Emulsion Preparations," HAPPI 28(4), pp. 88-128 (1991); J. Smid-Korbar et al., "Efficiency and usability of silicone surfactants in emulsions," *Provisional Communication, International Journal of Cosmetic Science*, 12, 135-139 (1990); and D. G. Krzysik et al., "A New Silicone Emulsifier For Water-in-Oil Systems," *Drug and Cosmetic Industry*, vol. 146(4), pp. 28-81 (April 1990).

Among the non-silicone-containing emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Other suitable emulsifiers are described, for example, in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973.

Nonlimiting examples of these non-silicone-containing emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

2) Oil-in-Water Emulsions

Other preferred topical carriers include oil-in-water emulsions, having a continuous aqueous phase and a hydrophobic, water-insoluble phase ("oil phase") dispersed therein. The "oil phase" can contain oil, silicone or mixtures thereof, and includes but is not limited to the oils and silicones described above in the section on water-in-silicone emulsions. The distinction of whether the emulsion is characterized as an oil-in-water or silicone-in-water emulsions is a function of whether the oil phase is composed of primarily oil or silicone. The water phase of these emulsions consists primarily of water, but can also contain various other ingredients such as those water phase ingredients listed in the above section on water-in-silicone emulsion. The preferred oil-in-water emulsions comprises from about 25% to about 98%, preferably from about 65% to about 95%, more preferably from about 70% to about 90% water by weight of the total composition.

In addition to a continuous water phase and dispersed oil or silicone phase, these oil-in-water compositions also comprise an emulsifier to stabilize the emulsion. Emulsifiers useful herein are well known in the art, and include nonionic, anionic, cationic, and amphoteric emulsifiers. Non-limiting examples of emulsifiers useful in the oil-in-water emulsions of this invention are given in *McCutcheon's, Detergents and Emulsifiers*, North American Edition (1986), published by Allured Publishing Corporation; U.S. Pat. No. 5,011,681; U.S. Pat. No. 4,421,769; and U.S. Pat. No. 3,755,560; these references are incorporated herein by reference in their entirety Composition Forms The topical compositions of the subject invention, including but not limited to lotions, milks, mousses, serums, sprays, aerosols, foams, sticks, pencils, gels, creams and ointments, may comprise a dermatologically acceptable emollient. Such compositions preferably contain from about 2% to about 50% of the emollient. As used herein, "emollient" refers to a material useful for the prevention or relief of dryness, as well as for the protection of the skin. A wide variety of suitable emollients are known and may be used herein. Sagarin, *Cosmetics, Science and Technology*, 2nd Edition, Vol. 1, pp. 32-43 (1972), incorporated herein by reference, contains numerous examples of materials suitable as an emollient. A preferred emollient is glycerin. Glycerin is preferably used in an amount of from about 0.001 to about 20%, more preferably from about 0.01 to about 15%, and most preferably from about 0.1 to about 10%.

Ointments of the present invention may comprise a simple carrier base of animal or vegetable oils or semi-solid hydrocarbons (oleaginous); absorption ointment bases which absorb water to form emulsions; or water soluble carriers, e.g., a water soluble solution carrier. Ointments may further comprise a thickening agent, such as described in Sagarin, *Cosmetics, Science and Technology*, 2nd Edition, Vol. 1, pp. 72-73 (1972), incorporated herein by reference, and/or an emollient.

Compositions of this invention useful for cleansing ("cleansers") are formulated with a suitable carrier, e.g., as described above, and from about 1% to about 90% of a dermatologically acceptable surfactant.

The physical form of the cleansing compositions is not critical. The compositions can be, for example, formulated as toilet bars, liquids, shampoos, bath gels, hair conditioners, hair tonics, pastes, or mousses. Toilet bars are most preferred since this is the form of cleansing agent most commonly used to wash the skin. Rinse-off cleansing compositions, such as shampoos, require a delivery system adequate to deposit sufficient levels of actives on the skin and scalp. A preferred delivery system involves the use of insoluble complexes. For a more complete disclosure of such delivery systems, see U.S. Pat. No. 4,835,148, Barford et al., issued May 30, 1989.

The compositions of the present invention may also be in the form of cosmetics. Suitable cosmetic forms include, but are not limited to, foundations, lipsticks, rouges, mascaras, and the like. Such cosmetic products may include conventional ingredients such as oils, colorants, pigments, emollients, fragrances, waxes, stabilizers, and the like. Exemplary carriers and such other ingredients which are suitable for use herein are described, for example, in copending patent application Ser. No. 08/430,961, filed on Apr. 28, 1995 in the names of Marcia L. Canter, Brain D. Barford, and Brian D. Hofrichter.

B. Optional Components

The compositions of the present invention may contain a variety of other ingredients such as are conventionally used in a given product type provided that they do not unacceptably alter the benefits of the invention.

In a preferred embodiment, where the composition is to be in contact with human keratinous tissue, the optional components should be suitable for application to keratinous tissue, that is, when incorporated into the composition they are suitable for use in contact with human keratinous tissue without undue toxicity, incompatibility, instability, allergic response, and the like within the scope of sound medical judgment. The *CTFA Cosmetic Ingredient Handbook*, Second Edition (1992) describes a wide variety of nonlimiting cosmetic and pharmaceutical ingredients commonly used in the skin care industry, which are suitable for use in the compositions of the present invention. Examples of these ingredient classes include: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, antifoaming agents, antimicrobial agents (e.g., iodopropyl butylcarbamate), antioxidants (e.g. BHT, BHA, tocopherol), binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine, pyridoxine), skin-conditioning agents (e.g., humectants, including miscellaneous and occlusive), skin soothing and/or healing agents (e.g., panthenol and derivatives such as ethyl panthenol, aloe vera, pantothenic acid and its derivatives, allantoin, bisabolol, and dipotassium glycyrrhizinate), skin treating agents (e.g., vitamin D compounds, mono-, di-, and tri-terpenoids, beta-ionol, cedrol), thickeners, and vitamins and vitamin derivatives.

In any embodiment of the present invention, however, the actives useful herein can be categorized by the benefit they provide or by their postulated mode of action. However, it is to be understood that the actives useful herein can in some instances provide more than one benefit or operate via more than one mode of action. Therefore, classifications herein are made for the sake of convenience and are not intended to limit the active to that particular application or applications listed.

1) Desquamation Actives

A safe and effective amount of a desquamation active may be added to the compositions of the present invention, preferably from about 0.1% to about 10%, more preferably from about 0.2% to about 5%, even more preferably from about 0.5% to about 4%, by weight of the composition. Desquamation actives enhance the skin appearance benefits of the present invention. For example, the desquamation actives tend to improve the texture of the skin (e.g., smoothness). One desquamation system that is suitable for use herein contains sulfhydryl compounds and zwitterionic surfactants and is described in U.S. Pat. No. 5,681,852, to Bissett, incorporated herein by reference. Another desquamation system that is suitable for use herein contains salicylic acid and zwitterionic surfactants and is described in U.S. Pat. No. 5,652,228 to Bissett, incorporated herein by reference. Zwitterionic surfactants such as described in these applications are also useful as desquamatory agents herein, with cetyl betaine being particularly preferred.

2) Anti-Acne Actives

The compositions of the present invention may comprise a safe and effective amount of one or more anti-acne actives. Examples of useful anti-acne actives include resorcinol, sulfur, salicylic acid, erythromycin, zinc, etc. Further examples of suitable anti-acne actives are described in further detail in U.S. Pat. No. 5,607,980, issued to McAtee et al, on Mar. 4, 1997.

3) Anti-Wrinkle Actives/Anti-Atrophy Actives

The compositions of the present invention may further comprise a safe and effective amount of one or more anti-wrinkle actives or anti-atrophy actives. Exemplary anti-wrinkle/anti-atrophy actives suitable for use in the compositions of the present invention include sulfur-containing D and L amino acids and their derivatives and salts, particularly the N-acetyl derivatives, a preferred example of which is N-acetyl-L-cysteine; thiols, e.g. ethane thiol; hydroxy acids (e.g., salicylic acid, glycolic acid), keto acids (e.g., pyruvic acid), ascorbic acid (vitamin C), phytic acid, lipoic acid; lysophosphatidic acid, skin peel agents (e.g., phenol and the like), flavonoids (e.g., flavanones, chalcones, isoflavones, flavones, etc.), stilbenes, cinnamates, resveratrol, kinetin, zeatin, dimethylaminoethanol, peptides from natural sources (e.g., soy peptides), salts of sugar acids (e.g., Mn gluconate), terpene alcohols (e.g., farnesol), peptides and retinoids which enhance the keratinous tissue appearance benefits of the present invention, especially in regulating keratinous tissue condition, e.g., skin condition, and vitamin B compounds (e.g., thiamine (vitamin B1), pantothenic acid (vitamin B5), carnitine (vitamin Bt), riboflavin (vitamin B2), cobalamine (vitamin B12), pangamic acid or diisopropylamine dichloroacetate (vitamin B15's), and their derivatives and salts (e.g., HCl salts or calcium salts)).

a) Retinoids

The compositions of this invention may contain a safe and effective amount of a retinoid, such that the resultant composition is safe and effective for regulating keratinous tissue condition, preferably for regulating visible and/or tactile discontinuities in skin, more preferably for regulating signs of skin aging. The compositions preferably contain from about 0.001% to about 10%, more preferably from about 0.005% to about 2%, even more preferably from about 0.01% to about 1%, still more preferably from about 0.01% to about 0.5%, by weight of the composition, of the retinoid. The optimum concentration used in a composition will depend on the specific retinoid selected since their potency does vary considerably.

As used herein, "retinoid" includes all natural and/or synthetic analogs of Vitamin A or retinol-like compounds which possess the biological activity of Vitamin A in the skin as well as the geometric isomers and stereoisomers of these compounds. The retinoid is preferably selected from retinol, retinol esters (e.g., $C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid), or mixtures thereof. More preferably the retinoid is a retinoid other than retinoic acid. These compounds are well known in the art and are commercially available from a number of sources, e.g., Sigma Chemical Company (St. Louis, Mo.), and Boerhinger Mannheim (Indianapolis, Ind.). Other retinoids which are useful herein are described in U.S. Pat. No. 4,677,120, issued Jun. 30, 1987 to Parish et al.; U.S. Pat. No. 4,885,311, issued Dec. 5, 1989 to Parish et al.; U.S. Pat. No. 5,049,584, issued Sep. 17, 1991 to Purcell et al.; U.S. Pat. No. 5,124,356, issued Jun. 23, 1992 to Purcell et al.; and Reissue 34,075, issued Sep. 22, 1992 to Purcell et al. Other suitable retinoids are tocopheryl-retinoate [tocopherol ester of retinoic acid (trans- or cis-), adapalene {6-[3-(1-adamantyl)-4-methoxyphenyl]-2-naphthoic acid}, and tazarotene (ethyl 6-[2-(4,4-dimethylthiochroman-6-yl)-ethynyl]nicotinate). Preferred retinoids are retinol, retinyl palmitate, retinyl acetate, retinyl propionate, retinal and combinations thereof. More preferred is retinyl propionate, used most preferably from about 0.1% to about 0.3%.

b) Peptides

The compositions of the present invention may contain a safe and effective amount of a peptide, including but not limited to, di-, tri-, tetra-, and penta-peptides and derivatives. The compositions contain preferably from about $1\times10^{-6}$% to about 20%, more preferably from about $1\times10^{-6}$% to about 10%, even more preferably from about $1\times10^{-5}$% to about 5%, by weight of the composition.

As used herein, "peptide" refers to peptides containing ten or fewer amino acids and their derivatives, isomers, and complexes with other species such as metal ions (e.g., copper, zinc, manganese, magnesium, and the like). As used herein, peptide refers to both naturally occurring and synthesized peptides. Also useful herein are naturally occurring and commercially available compositions that contain peptides. Preferred peptides contain at least one basic amino acid (e.g., histidine, lysine, arginine). More preferred peptides are the dipeptide camosine (beta-ala-his), the tripeptide gly-his-lys, the tripeptide his-gly-gly, the tripeptide gly-gly-his, the tripeptide gly-his-gly, the pentapeptide lys-thr-thr-lys-ser, and metal complexes of the above, e.g., copper complex of the tripeptide his-gly-gly (also known as lamin). Other suitable peptides include Peptide CK (arg-lys-arg); Peptide CK+ (ac-arg-lys-arg-$NH_2$); and Peptide E, arg-ser-arg-lys. A preferred commercially available tripeptide derivative-containing composition is Biopeptide CL®, which contains 100 ppm of palmitoyl-gly-his-lys and is commercially available from Sederma, France. A preferred commercially available pentapeptide derivative-containing composition is Matrixyl®, which contains 100 ppm of palmitoyl-lys-thr-thr-lys-ser and is commercially available from Sederma, France. Peptide derivatives useful herein include lipophilic derivatives, preferably palmitoyl derivatives. Preferably, the peptide is selected from palmitoyl-lys-thr-thr-lys-ser, palmitoyl-gly-his-lys, their derivatives, and combinations thereof.

c) Hydroxy Acids

The compositions of the present invention may contain a safe and effective amount of a Hydroxy Acid. Preferred hydroxy acids for use in the compositions of the present invention include alpha hydroxy acids such as lactic acid and glycolic acid. When present in the compositions of the present invention, the hydroxy acid is preferably used in an amount of from about 0.01% to about 50%, more preferably from about 0.1% to about 10%, and still more preferably from about 0.5% to about 2%.

4) Water-Soluble Vitamins

The compositions of the present invention may contain a safe and effective amount of one or more water-soluble vitamins. Examples of water-soluble vitamins include, but are not limited to, water-soluble versions of vitamin B, vitamin B derivatives, vitamin C, vitamin C derivatives, vitamin K, vitamin K derivatives, vitamin D, vitamin D derivatives, vitamin E, vitamin E derivatives, and mixtures thereof. The vitamin compounds may be included as the substantially pure material, or as an extract obtained by suitable physical and/or chemical isolation from natural (e.g., plant) sources. When vitamin compounds are present in the compositions of the instant invention, the compositions preferably contain from about 0.0001% to about 50%, more preferably from about 0.001% to about 10%, still more preferably from about 0.01% to about 5%, and still more preferably from about 1% to about 5%, by weight of the composition, of the vitamin compound.

a) Vitamin $B_3$ Compounds

The compositions of the present invention may contain a safe and effective amount of a vitamin $B_3$ compound. When vitamin $B_3$ compounds are present in the compositions of the instant invention, the compositions preferably contain from about 0.01% to about 50%, more preferably from about 0.1% to about 10%, still more preferably from about 1% to about 10%, and still more preferably from about 2% to about 5%, by weight of the composition, of the vitamin $B_3$ compound.

As used herein, "vitamin $B_3$ compound" means a compound having the formula:

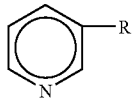

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

Exemplary derivatives of the foregoing vitamin $B_3$ compounds include nicotinic acid esters, including non-vasodilating esters of nicotinic acid (e.g., niacinamide), nicotinyl amino acids, nicotinic acid N-oxide and niacinamide N-oxide.

5) Anti-Oxidants/Radical Scavengers

The compositions of the present invention may include a safe and effective amount of an anti-oxidant/radical scavenger, preferably from about 0.001% to about 10%, more preferably from about 0.01% to about 5%, of the composition. The anti-oxidant/radical scavenger is especially useful for providing protection against UV radiation which can cause increased scaling or texture changes in the stratum corneum and against other environmental agents which can cause skin damage.

Anti-oxidants/radical scavengers such as ascorbic acid (vitamin C) and its salts, ascorbic acid derivatives (e.g., magnesium ascorbyl phosphate, sodium ascorbyl phosphate, ascorbyl glucoside), tocotrienols, butylated hydroxy benzoic acid salts, butylated hydroxy benzoic acids and their salts, 6-hydroxy-2,5,7,8-tetramethylchroman-2-carboxylic acid (commercially available under the tradename Trolox$^R$), gallic acid and its alkyl esters, especially propyl gallateuric acid salts, sorbic acid salts, dihydroxy fumaric acid salts, lysine, methionine, proline, superoxide dismutase, silymarin, tea extracts, grape skin/seed extracts, melanin, and rosemary extracts may be used. A preferred anti-oxidants/radical scavenger is vitamin E and derivatives.

6) Anti-Inflammatory Agents

A safe and effective amount of an anti-inflammatory agent may be added to the compositions of the present invention, preferably from about 0.01% to about 10%, more preferably from about 0.1% to about 5%, of the composition. The anti-inflammatory agent enhances the skin appearance benefits of the present invention, e.g., such agents contribute to a more uniform and acceptable skin tone or color. The exact amount of anti-inflammatory agent to be used in the compositions will depend on the particular anti-inflammatory agent utilized since such agents vary widely in potency.

Steroidal anti-inflammatory agents, including but not limited to, corticosteroids such as hydrocortisone.

A second class of anti-inflammatory agents, which is useful in the compositions, includes the nonsteroidal anti-inflammatory agents. The varieties of compounds encompassed by this group are well known to those skilled in the art. For detailed disclosure of the chemical structure, synthesis, side effects, etc. of non-steroidal anti-inflammatory agents, one may refer to standard texts, including *Anti-inflammatory and Anti-Rheumatic Drugs*, K. D. Rainsford, Vol. I-III, CRC Press, Boca Raton, (1985), and *Anti-inflammatory Agents, Chemistry and Pharmacology*, 1, R. A. Scherrer, et al., Academic Press, New York (1974). Specific non-steroidal anti-inflammatory agents useful in the composition invention include, but are not limited to, salicylates, flufenamic acid, etofenamate, aspirin, and mixtures thereof.

Finally, so-called "natural" anti-inflammatory agents are useful in methods of the present invention. Such agents may suitably be obtained as an extract by suitable physical and/or chemical isolation from natural sources (e.g., plants, fungi, by-products of microorganisms). For example, candelilla wax, alpha-bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, red clover extract, and sea whip extract, may be used.

Additional anti-inflammatory agents useful herein include allantoin and compounds of the Licorice (the plant genus/species *Glycyrrhiza glabra*) family, including glycyrrhetic acid, glycyrrhizic acid, and derivatives (e.g., salts and esters). Suitable salts of the foregoing compounds include metal and ammonium salts. Suitable esters include $C_2$-$C_{24}$ saturated or unsaturated esters of the acids, preferably $C_{10}$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

7) Flavonoids

The compositions of the present invention may contain a safe and effective amount of an oil or water-soluble flavonoid. A preferred example of a water soluble flavonoid is o-glycoside.

Oil-soluble flavonoid compounds are broadly disclosed in U.S. Pat. Nos. 5,686,082 and 5,686,367, both of which are herein incorporated by reference. Examples of flavonoids suitable for use in the present invention are flavanones selected from the group consisting of unsubstituted flavanones, mono-substituted flavanones, and mixtures thereof; chalcones selected from the group consisting of unsubstituted chalcones, mono-substituted chalcones, di-substituted chalcones, tri-substituted chalcones, and mixtures thereof; flavones selected from the group consisting of unsubstituted flavones, mono-substituted flavones, di-substituted flavones, and mixtures thereof; one or more isoflavones; coumarins selected from the group consisting of unsubstituted coumarins, mono-substituted coumarins, di-substituted coumarins, and mixtures thereof; chromones selected from the group consisting of unsubstituted chromones, mono-substituted chromones, di-substituted chromones, and mixtures thereof; one or more dicoumarols; one or more chromanones; one or more chromanols; isomers (e.g., cis/trans isomers) thereof; and mixtures thereof. By the term "substituted" as used herein means flavonoids wherein one or more hydrogen atom of the flavonoid has been independently replaced with hydroxyl, C1-C8 alkyl, C1-C4 alkoxyl, O-glycoside, and the like or a mixture of these substituents. Preferred for use herein are flavones and isoflavones, in particular unsubstituted isoflavone, daidzein (7,4'-dihydroxy isoflavone), genistein (5,7,4'-trihydroxy isoflavone), equol (7,4'-dihydroxy isoflavan), 5,7-dihydroxy-4'-methoxy isoflavone, soy isoflavones (a mixture extracted from soy), and mixtures thereof.

They can be synthetic materials or obtained as extracts from natural sources (e.g., plants). The naturally sourced material can also further be derivatized (e.g., an ester or ether derivative prepared following extraction from a natural source). Flavonoid compounds useful herein are commercially available from a number of sources, e.g., Indofine Chemical Company, Inc. (Somerville, N.J.), Steraloids, Inc. (Wilton, N.H.), and Aldrich Chemical Company, Inc. (Milwaukee, Wis.).

Mixtures of the above flavonoid compounds may also be used.

The herein described flavonoid compounds are preferably present in the instant invention at concentrations of from about 0.01% to about 20%, more preferably from about 0.1% to about 10%, and most preferably from about 0.5% to about 5%.

8) Anti-Cellulite Agents

The compositions of the present invention may contain a safe and effective amount of an anti-cellulite agent. Suitable agents may include, but are not limited to, xanthine compounds (e.g., theophylline, theobromine, aminophylline, Genistein, and green tea. Anti-cellulite agents preferably comprise from about 0.1% and to about 10% by weight of the composition.

9) Tanning Actives

The compositions of the present invention may contain a safe and effective amount of a tanning active, preferably from about 0.1% to about 20% of dihydroxyacetone as an artificial tanning active. Dihydroxyacetone, which is also known as DHA or 1,3-dihydroxy-2-propanone, is a white to off-white, crystalline powder.

10) Skin Lightening Agents

The compositions of the present invention may comprise a skin lightening agent. When used, the compositions preferably comprise from about 0.1% to about 10%, more preferably from about 0.2% to about 7.5%, also preferably from about 0.5% to about 5%, by weight of the composition, of a skin lightening agent. Suitable skin lightening agents include those known in the art, including kojic acid, arbutin, tranexamic acid, phytosterols, ascorbic acid and derivatives, e.g., magnesium ascorbyl phosphate or sodium ascorbyl phosphate or other salts of ascorbyl phosphate, ascorbyl glucoside, and the like. Other skin lightening materials suitable for use herein include undecylenoyl phenylalanine (Sepiwhite® from SEPPIC), aloesin, Actiwhite® (Cognis), Emblica® (Rona), and Azeloglicina (Sinerga) and extracts (e.g. mulberry extract, placental extract).

a) Phytosterol

The topical compositions of the present invention comprise a safe and effective amount of one or more phytosterols selected from the group consisting of β-sitosterol, campesterol, brassicasterol, Δ5-avennasterol, lupenol, α-spinasterol, stigmasterol, their derivatives, analogs, and combinations thereof. More preferably, the phytosterol is selected from the group consisting of β-sitosterol, campesterol, brassicasterol, stigmasterol, their derivatives, and combinations thereof. Even more preferably, the phytosterol is selected from the group consisting of β-sitosterol, campesterol, brassicasterol, stigmasterol, and combinations thereof.

Phytosterols can be synthetic or natural in origin and can be used as essentially pure compounds or mixtures of compounds (e.g., extracts from natural sources). Phytosterols are generally found in the unsaponifiable portion of vegetable oils and fats and are available as free sterols, acetylated derivatives, sterol esters, ethoxylated or glycosidic derivatives. More preferably, the phytosterols are free sterols. As used herein, "phytosterol" includes isomers and tautomers of such and is commercially available from Aldrich Chemical Company (Milwaukee, Wis.), Sigma Chemical Company (St. Louis, Mo.), and Cognis Corportation. In the compositions of the present invention, the phytosterol preferably comprises from about 0.01% to about 10%, by weight of the composition, more preferably from about 0.1% to about 7.5%, and most preferably from about 0.2% to about 5%.

11) Skin Soothing and Skin Healing Actives

A safe and effective amount of a skin soothing or skin healing active may be added to the present composition, preferably, from about 0.1% to about 30%, more preferably from about 0.5% to about 20%, still more preferably from about 0.5% to about 10%, by weight of the composition formed. Skin soothing or skin healing actives suitable for use herein include panthenoic acid derivatives (including panthenol, dexpanthenol, ethyl panthenol), aloe vera, allantoin, and dipotassium glycyrrhizinate.

12) Antimicrobial and Antifungal Actives

The compositions of the present invention may comprise an antimicrobial or antifungal active. Such actives are capable of destroying microbes, preventing the development of microbes or preventing the pathogenic action of microbes. A safe and effective amount of an antimicrobial or antifungal active may be added to the present compositions, preferably, from about 0.001% to about 10%, more preferably from about 0.01% to about 5%, and most preferably from about 0.05% to about 2%.

Examples of antimicrobial and antifungal actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, methyl paraben, ethyl paraben, butyl paraben, Glydant®, Glydant Plus®, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Preferred examples of actives useful herein include those selected from the group consisting of methyl paraben, ethyl paraben, butyl paraben, Glydant®, Glydant Plus®, salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neocycin sulfate, and mixtures thereof 13) Chelators The compositions of the present invention may also comprise a safe and effective amount of a chelator or chelating agent. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation that can contribute to excessive scaling or skin texture changes and against other environmental agents, which can cause skin damage.

A safe and effective amount of a chelating agent may be added to the compositions of the subject invention, preferably from about 0.1% to about 10%, more preferably from about 1% to about 5%, of the composition. Exemplary chelators that are useful herein are disclosed in U.S. Pat. No. 5,487,884, issued Jan. 30, 1996 to Bissett et al.; International Publication No. 91/16035, Bush et al., published Oct. 31, 1995; and International Publication No. 91/16034, Bush et al., published Oct. 31, 1995. Preferred chelators useful in compositions of the subject invention are furildioxime and derivatives.

14) Sunscreen Actives

Exposure to ultraviolet light can result in excessive scaling and texture changes of the stratum corneum. Therefore, the compositions of the subject invention may optionally contain a sunscreen active. As used herein, "sunscreen active" includes both sunscreen agents and physical sunblocks. Suitable sunscreen actives may be organic or inorganic.

Non-limiting examples of inorganic sunscreens useful herein include the following metallic oxides; titanium dioxide having an average primary particle size of from about 15 nm to about 100 nm, zinc oxide having an average primary particle size of from about 15 nm to about 150 nm, zirconium oxide having an average primary particle size of from about 15 nm to about 150 nm, iron oxide having an average primary particle size of from about 15 nm to about 500 nm, and mixtures thereof. When used herein, the inorganic sunscreens are present in the amount of from about 0.1% to about 20%, preferably from about 0.5% to about 10%, more preferably from about 1% to about 5%, by weight of the composition.

A wide variety of conventional sunscreen actives are suitable for use herein. Sagarin, et al., at Chapter VIII, pages 189 et seq., of *Cosmetics Science and Technology* (1972), discloses numerous suitable actives. Specific suitable sunscreen actives include, for example: p-aminobenzoic acid, its salts and its derivatives (ethyl, isobutyl, glyceryl esters; p-dimethylaminobenzoic acid); anthranilates (i.e., o-aminobenzoates; methyl, menthyl, phenyl, benzyl, phenylethyl, linalyl, terpinyl, and cyclohexenyl esters); salicylates (amyl, phenyl, octyl, benzyl, menthyl, glyceryl, and di-pro-pyleneglycol esters); cinnamic acid derivatives (menthyl and benzyl esters, a-phenyl cinnamonitrile; butyl cinnamoyl pyruvate); hydroxy- or methoxy-substituted benzophenones; benzophenones (oxybenzene, sulisobenzone, dioxybenzone, benzoresorcinol, 2,2',4,4'-tetrahydroxybenzophenone, 2,2'-dihydroxy-4,4'-dimethoxybenzophenone, octabenzone; 4-isopropyldibenzoylmethane; butylmethoxydibenzoylmethane; etocrylene; octocrylene; [3-(4'-methylbenzylidene bornan-2-one) and 4-isopropyl-di-benzoyl-methane.

Of these, 2-ethylhexyl-p-methoxycinnamate (commercially available as PARSOL MCX), 4,4'-t-butyl methoxydibenzoyl-methane (commercially available as PARSOL 1789), 2-hydroxy-4-methoxybenzophenone, octyldimethyl-p-aminobenzoic acid, 2,2-dihydroxy-4-methoxybenzophenone, ethyl-4-(bis(hydroxy-propyl))aminobenzoate, 2-ethylhexyl-2-cyano-3,3-diphenylacrylate, 2-ethylhexylsalicylate, glyceryl-p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, octocrylene, butylmethoxydibenzoylmethane and mixtures of these compounds, are preferred.

Also useful in the compositions are sunscreen actives having, in a single molecule, two distinct chromophore moieties which exhibit different ultra-violet radiation absorption spectra. One of the chromophore moieties absorbs predominantly in the UVB radiation range and the other absorbs strongly in the UVA radiation range.

Especially preferred sunscreen actives include 4,4'-t-butylmethoxydibenzoylmethane, 2-ethylhexyl-p-methoxycinnamate, phenyl benzimidazole sulfonic acid, 2-ethylhexyl Salicylate, octocrylene, zinc oxide, and titanium dioxide, and mixtures thereof.

When present in the composition, a safe and effective amount of the sunscreen active is used, typically from about 1% to about 25%, more typically from about 2% to about 25% by weight of the composition. Exact amounts will vary depending upon the sunscreen chosen and the desired Sun Protection Factor (SPF).

15) Particulate Material

The compositions of the present invention may, in some embodiments, contain one or more particulate materials. Nonlimiting examples of particulate materials useful in the present invention include colored and uncolored pigments, interference pigments, inorganic powders, organic powders, composite powders, optical brightener particles, and combinations thereof. These particulates can be platelet shaped, spherical, elongated or needle-shaped, or irregularly shaped, surface coated or uncoated, porous or non-porous, charged or uncharged, and can be added to the current compositions as a powder or as a pre-dispersion. These particulate materials may provide a wide range of functions, including by not limited to modifying skin feel, masking the appearance of certain skin characteristics such as blotchy areas, age spots, freckles, fine lines, wrinkles, and pores, absorbing excess skin sebum/oils, reducing skin shine, improving application properties of the composition, masking the color of other components of the composition, filling in skin pores, lines and wrinkles, and reducing migration of liquid materials on the skin. Preferably, particulate materials are present in the composition in levels of from about 0.01% to about 20%, more preferably from about 0.05% to about 10%, still more preferably from about 0.1% to about 5%, by weight of the composition. There are no specific limitations as to the pigment, colorant or filler powders used in the composition.

Particulate materials useful herein include but are not limited to bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, sericite, aluminum oxide, silicone resin, barium sulfate, calcium carbonate, cellulose acetate, PTFE, polymethyl methacrylate, starch, modified starches such as aluminun starch octenyl succinate, silk, glass, and mixtures thereof. Preferred organic powders/fillers include, but are not limited to, polymeric particles chosen from the methylsilsesquioxane resin microspheres such as for example those sold by Toshiba silicone under the name Tospearl 145A; microspheres of polymethylmethacrylates such as those sold by Seppic under the name Micropearl M 100; the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat C05, polystyerene microspheres such as for example those sold by Dyno Particles under the name Dynospheres, ethylene acrylate copolymer sold by Kobo under the name FloBead EA209, PTFE, polypropylene, aluminium starch ocetenylsuccinate such as those sold by National Starch under the name Dry Flo, microspheres of polyethylene such as those sold by Equistar under the name of Microthene FN510-00, silicone resin, polymethylsilsesquioxane silicone polymer, platelet shaped powder made from L-lauroyl lysine, and mixtures thereof. Especially preferred are spherical powders with an average primary particle size from 0.1 to 75 microns, preferably from 0.2 to 30 microns.

Also useful herein are interference pigments. Interference pigments, for purposes of the present specification are defined as thin platelike layered particles having a two or more layers of controlled thickness with different refractive indices that yield a characteristic reflected color from the interference of typically two, but occasionally, more, light reflections, form different layers of the platelike particle. The most common examples of interference pigments are micas layered with about 50-300 nm films of $TiO_2$, $Fe_2O_3$, silica, tin oxide, and/or $Cr_2O_3$. Such pigments are often peralescent. Pearl pigments reflect, refract and transmit light because of the transparency of pigment particles and the large difference in the refractive index of mica platelets and, for example, the titanium dioxide coating. Useful intereference pigments are available commercially from a wide variety of suppliers, for example, Rona (Timiron™ and Dichrona™), Presperse (Flonac™), Englehard (Duochrome™), Kobo (SK45-R and SK-45-G), BASF (Sicopearls) and Eckart (e.g. Prestige Silk Red). Especially preferred are interference pigments with smaller particle sizes, with an average diameter of individual particles less than about 75 microns in the longest direction, preferably with an average diameter less than about 50 microns.

Other pigments useful in the present invention provide color primarily through selective absorption of specific wavelengths of visible light, and include inorganic pigments, organic pigments and combinations thereof. Examples of useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example $TiO_2$, ZnO, or $ZrO_2$, are commercially available from a number of sources. One example of a suitable particulate material contains the material available from U.S. Cosmetics (TRONOX $TiO_2$ series, SAT-T CR837, a rutile $TiO_2$). Particularly preferred are charged dispersions of titanium dioxide, as are disclosed in U.S. Pat. No. 5,997,887, to Ha, et al., incorporated herein by reference.

Preferred colored or uncolored non-interference-type pigments have a primary average particle size of from about 10 nm to about 100,000 nm, more preferably from about 20 nm to about 5,000 nm, most preferably from about 20 nm to about 1000 nm. Mixtures of the same or different pigment/powder having different particle sizes are also useful herein (e.g., incorporating a $TiO_2$ having a primary particle size of from about 100 nm to about 400 nm with a $TiO_2$ having a primary particle size of from about 10 nm to about 50 nm).

The pigments/powders of the current invention can be surface treated to provide added stability of color and/or for ease of formulation. Non-limiting examples of suitable coating materials include silicones, lecithin, amino acids, metal soaps, polyethylene and collagen. These surface treatments may be hydrophobic or hydrophilic, with hydrophobically treatments being preferred. Particularly useful hydrophobic pigment treatments include polysiloxane treatments such as those disclosed in U.S. Pat. No. 5,143,722, incorporated herein by reference in its entirety.

16) Conditioning Agents

The compositions of the present invention may comprise a conditioning agent selected from the group consisting of humectants, moisturizers, or skin conditioners. A variety of these materials can be employed and each can be present at a level of from about 0.01% to about 40%, more preferably from about 0.1% to about 30%, and most preferably from about 0.5% to about 15%, by weight of the composition. Non-limiting examples of conditioning agents include guanidine; urea; glycolic acid and glycolate salts (e.g. ammonium and quaternary alkyl ammonium); salicylic acid; lactic acid and lactate salts (e.g., ammonium and quaternary alkyl ammonium); aloe vera in any of its variety of forms (e.g., aloe vera gel); polyhydroxy alcohols such as sorbitol, mannitol, xylitol, erythritol, glycerol, hexanetriol, butanetriol, propylene glycol, butylene glycol, hexylene glycol and the like; polyethylene glycols; sugars (e.g., melibiose) and starches; sugar and starch derivatives (e.g., alkoxylated glucose, fucose, glucosamine); hyaluronic acid; lactamide monoethanolamine; acetamide monoethanolamine; panthenol; allantoin; and mixtures thereof. Also useful herein are the propoxylated glycerols described in U.S. Pat. No. 4,976,953, to Orr et al, issued Dec. 11, 1990, incorporated herein by reference.

Also useful are various $C_1$-$C_{30}$ monoesters and polyesters of sugars and related materials. These esters are derived from a sugar or polyol moiety and one or more carboxylic acid moieties. Such ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al, issued Apr. 26, 1994; U.S. Pat. No. No. 5,306,515, to Letton et al, issued Apr. 26, 1994; U.S. Pat. No. 5,305,514, to Letton et al, issued Apr. 26, 1994; U.S. Pat. No. 4,797,300, to Jandacek et al, issued Jan. 10, 1989; U.S. Pat. No. 3,963,699, to Rizzi et al, issued Jun. 15, 1976; U.S. Pat. No. 4,518,772, to Volpenhein, issued May 21, 1985; and U.S. Pat. No. 4,517,360, to Volpenhein, issued May 21, 1985.

Preferably, the conditioning agent is selected from the group consisting of urea, guanidine, sucrose polyester, panthenol, allantoin, and combinations thereof.

Thickening Agent (Including Thickeners and Gelling Agents)

The compositions of the present invention can comprise one or more thickening agents, preferably from about 0.1% to about 10%, more preferably from about 0.1% to about 5%, and most preferably from about 0.25% to about 4%, by weight of the composition. The compositions of the present invention may also contain mixtures of thickening agents.

Nonlimiting classes of thickening agents include those selected from the group consisting of:

a) Carboxylic Acid Polymers

Non-limiting examples of commercially available carboxylic acid polymers useful herein include the carbomers, which are homopolymers of acrylic acid crosslinked with allyl ethers of sucrose or pentaerytritol. The carbomers are available as the Carbopol® 900 series from B.F. Goodrich (e.g., Carbopol® 954). In addition, other suitable carboxylic acid polymeric agents include copolymers of $C_{10-30}$ alkyl acrylates with one or more monomers of acrylic acid, methacrylic acid, or one of their short chain (i.e., $C_{1-4}$ alcohol) esters, wherein the crosslinking agent is an allyl ether of sucrose or pentaerytritol. These copolymers are known as acrylates/$C_{10-30}$ alkyl acrylate crosspolymers and are commercially available as Carbopol® 1342, Carbopol® 1382, Pemulen TR-1, and Pemulen TR-2, from B.F. Goodrich b) Crosslinked Polyacrylate Polymers Non-limiting examples of useful crosslinked nonionic polyacrylate polymers and crosslinked cationic polyacrylate polymers are those described in U.S. Pat. No. 5,100,660, to Hawe et al, issued Mar. 31, 1992; U.S. Pat. No. 4,849,484, to Heard, issued Jul. 18, 1989; U.S. Pat. No. 4,835,206, to Farrar et al, issued May 30, 1989; U.S. Pat. No. 4,628,078 to Glover et al issued Dec. 9, 1986; U.S. Pat. No. 4,599,379 to Flesher et al issued Jul. 8, 1986; and EP 228,868, to Farrar et al, published Jul. 15, 1987, all of which are incorporated herein.

c) Polyacrylamide Polymers

A non-limiting example of a polyacrylamide nonionic polymer useful herein is one given the CTFA designation polyacrylamide and isoparaffin and laureth-7, available under the Tradename Sepigel 305 from Seppic Corporation (Fairfield, N.J.).

Other polyacrylamide polymers useful herein include multi-block copolymers of acrylamides and substituted acrylamides with acrylic acids and substituted acrylic acids. Commercially available examples of these multi-block copolymers include Hypan SR150H, SS500V, SS500W, SSSA100H, from Lipo Chemicals, Inc., (Patterson, N.J.).

d) Polysaccharides

Nonlimiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl substituted celluloses. In these polymers, the hydroxy groups of the cellulose polymer is hydroxyalkylated (preferably hydroxyethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Examples of alkyl groups useful herein include those selected from the group consisting of stearyl, isostearyl, lauryl, myristyl, cetyl, isocetyl, cocoyl (i.e. alkyl groups derived from the alcohols of coconut oil), palmityl, oleyl, linoleyl, linolenyl, ricinoleyl, behenyl, and mixtures thereof. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation (Wilmington, Del.).

Other useful polysaccharides include scleroglucans comprising a linear chain of (1-3) linked glucose units with a (1-6) linked glucose every three units, a commercially available example of which is Clearogel™ CS11 from Michel Mercier Products Inc. (Mountainside, N.J.).

e) Gums

Nonlimiting examples of gelling agent gums include materials selected from the group consisting of acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

II. Composition Preparation

The compositions of the present invention are generally prepared by conventional methods such as are known in the art of making topical compositions. Such methods typically involve mixing of the ingredients in one or more steps to a relatively uniform state, with or without heating, cooling, application of vacuum, and the like. The compositions are preferably prepared such as to optimize stability (physical stability, chemical stability, photostability) and/or delivery of the active materials (e.g., dipalmitoyl hydroxyproline, hexamidine, sugar amine). This optimization may include appropriate pH exclusion of materials that can complex with the active agent and thus negatively impact stability or delivery (e.g., exclusion of contaminating iron), use of approaches to prevent complex formation (e.g., appropriate dispersing agents or dual compartment packaging), use of appropriate photostability approaches (e.g., incorporation of sunscreen/sunblock, use of opaque packaging or other similarly suitable packaging).

Appropriate pH values are dependent upon the stability requirements of the specific compositions used. However, most of the instant skin care compositions will have pH values between 4 and 8.

It has also been discovered that when incorporating the dialkanoyl hydroxyproline compounds in the water portion of the composition, it is advantageous to use the corresponding salt of said dialkanoyl hydroxyproline. This salt form of dialkanoyl hydroxyproline compounds could be purchased or made during processing of the composition of the present invention. If doing the later, this can be achieve by a separate salt forming step or make the salt in situ while processing the composition of the present invention. Either way, this is achieved by adding a sufficient amount of a basic reagent at a concentration necessary to convert a desired amount of the compound into its corresponding salt that readily is solubilized by water.

III. Methods for Regulating Keratinous Tissue Condition

The compositions of the present invention are useful for regulating a number of mammalian keratinous tissue conditions. Such regulation of keratinous tissue conditions includes prophylactic and therapeutic regulation. More specifically, such regulating methods are directed to, but are not limited to, thickening keratinous tissue (i.e., building the epidermis and/or dermis and/or subcutaneous layers of the skin and where applicable the keratinous layers of the nail and hair shaft), preventing, retarding, and/or treating atrophy of mammalian skin, softening and/or smoothing lips, hair and nails of a mammal, preventing, retarding, and/or treating itch of mammalian skin, preventing, retarding, and/or treating the appearance of dark under-eye circles and/or puffy eyes, preventing, retarding, and/or treating sallowness of mammalian skin, preventing, retarding, and/or treating sagging (i.e., glycation) of mammalian skin, preventing and/or retarding tanning of mammalian skin, desquamating, exfoliating, and/or increasing turnover in mammalian skin, reducing the size of pores in mammalian skin, regulating oily/shiny appearance of mammalian skin, preventing, retarding, and/or treating hyperpigmentation such as post-inflammatory hyperpigmentation, preventing, retarding, and/or treating the appearance of spider vessels and/or red blotchiness on mammalian skin, preventing, retarding, and/or treating fine lines and wrinkles of mammalian skin, preventing, retarding, and/or treating skin dryness (i.e., roughness, scaling, flaking) and preventing, retarding, and/or treating the appearance of cellulite in mammalian skin.

Applicants have surprisingly found that compositions consisting essentially of the select compounds and combinations of compounds of the present invention are useful for the above disclosed methods as well.

Regulating keratinous tissue condition involves topically applying to the keratinous tissue a safe and effective amount of a composition of the present invention. The amount of the composition that is applied, the frequency of application and the period of use will vary widely depending upon the level of dipalmitoyl hydroxyproline and other components of a given composition and the level of regulation desired, e.g., in light of the level of keratinous tissue damage present or expected to occur.

In a preferred embodiment, the composition is chronically applied to the skin. By "chronic topical application" is meant continued topical application of the composition over an extended period during the subject's lifetime, preferably for a period of at least about one week, more preferably for a period of at least about one month, even more preferably for at least about three months, even more preferably for at least about six months, and more preferably still for at least about one year. While benefits are obtainable after various maximum periods of use (e.g., five, ten or twenty years), it is preferred that chronic applications continue throughout the subject's lifetime. Typically applications would be on the order of about once per day over such extended periods, however application rates can vary from about once per week up to about three times per day or more.

A wide range of quantities of the compositions of the present invention can be employed to provide a skin appearance and/or feel benefit. Quantities of the present compositions, which are typically applied per application, are, in mg composition/cm$^2$ skin, from about 0.1 mg/cm$^2$ to about 20 mg/cm$^2$. A particularly useful application amount is about 0.5 mg/cm$^2$ to about 10 mg/cm$^2$.

Regulating keratinous tissue condition is preferably practiced by applying a composition in the form of a skin lotion, clear lotion, milky lotion, cream, gel, foam, ointment, paste, emulsion, spray, conditioner, tonic, cosmetic, lipstick, foundation, nail polish, after-shave, mousse, liquid solution, serum, or the like which is intended to be left on the skin or other keratinous tissue for some esthetic, prophylactic, therapeutic or other benefit (i.e., a "leave-on" composition). After applying the composition to the keratinous tissue (e.g., skin), it is preferably left on for a period of at least about 15 minutes, more preferably at least about 30 minutes, even more preferably at least about 1 hour, most preferably for at least several hours, e.g., up to about 12 hours. Any part of the external portion of the face, hair, and/or nails can be treated, e.g., face, lips, under-eye area, eyelids, scalp, neck, torso, arms, hands, legs, fingernails, toenails, scalp hair, eyelashes, eyebrows, etc. The application of the present compositions may be done using, e.g., the palms of the hands and/or fingers, an implement, e.g., a cotton ball, swab, pad etc.

Another approach to ensure a continuous exposure of the keratinous tissue to at least a minimum level of the combined actives is to apply the compound by use of a patch applied, e.g., to the face. Such an approach is particularly useful for problem skin areas needing more intensive treatment (e.g., facial crows feet area, frown lines, under eye area, and the like). The patch can be occlusive, semi-occlusive or non-occlusive. The combination composition can be contained within the patch or be applied to the skin prior to application of the patch. The patch can also include additional actives such as chemical initiators for exothermic reactions such as those described in PCT application WO 9701313 to Burkett et al. The patch can also contain a source of electrical energy (e.g., a battery) to, for example, increase delivery of the active agents. The patch is preferably left on the keratinous tissue for a period of at least about 5 minutes, more preferably at least about 15 minutes, more preferably still at least about 30 minutes, even more preferably at least about 1 hour, most preferably at night as a form of night therapy.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Examples 1-5

Moisturizing oil-in-water lotions/creams are prepared by conventional methods from the following components:

|  | Example 1 | Example 2 | Example 3 | Example 4 | Example 5 |
| --- | --- | --- | --- | --- | --- |
| Water Phase: | | | | | |
| Water | qs | qs | qs | qs | qs |
| Glycerin | 3 | 5 | 7 | 10 | 15 |
| Disodium EDTA | 0.1 | 0.1 | 0.05 | 0.1 | 0.1 |
| Methylparaben | 0.1 | 0.1 | 0.1 | 0.1 | 0.1 |
| Niacinamide | 2 | 0.5 | 3.5 | 3 | 5 |
| D-panthenol | 0.5 | 0.1 | 1.0 | 0.5 | 1.5 |
| Sodium Hydroxide | 0.001 | 0.002 | 0.001 | 0.001 | 0.001 |
| Benzyl alcohol | 0.25 | 0.25 | 0.25 | 0.25 | 0.25 |
| FD&C Red #40 | — | — | — | — | 0.0005 |
| FD&C Yellow #5 | — | — | — | — | 0.0010 |
| GLW75CAP-MP (75% aq. TiO2 dispersion)[1] | — | 0.5 | 0.5 | — | — |
| Hexamidine isethionate | 0.1 | 0.1 | — | 0.1 | — |
| Palmitoyl-pentapeptide[2] | 0.0002 | — | — | — | 0.0003 |
| N-acetyl glucosamine | 2 | — | 2 | — | 5 |
| Oil Phase: | | | | | |
| Isohexadecane | 3 | 3 | 3 | 4 | 3 |
| Isopropyl Isostearate | 1 | 0.5 | 1.3 | 1.5 | 1.3 |
| Sucrose polyester | 0.7 | — | 0.7 | 1 | 0.7 |
| Dipalmitoylhyroxyproline | 1 | 2 | 1 | 0.1 | 1 |
| Phytosterol | — | — | — | 0.5 | — |
| Retinyl propionate | — | — | — | 0.1 | — |
| Cetyl alcohol | 0.4 | 0.3 | 0.4 | 0.5 | 0.4 |
| Stearyl alcohol | 0.5 | 0.35 | 0.5 | 0.6 | 0.5 |
| Behenyl alcohol | 0.4 | 0.3 | 0.4 | 0.5 | 0.4 |
| PEG-100 stearate | 0.1 | 0.1 | 0.1 | 0.2 | 0.1 |
| Stearic Acid | 0.1 | 0.05 | 0.1 | 0.2 | 0.1 |
| Cetearyl glucoside | 0.1 | 0.1 | 0.1 | 0.25 | 0.1 |
| Thickener: | | | | | |
| Polyacrylamide/C13-14 isoparaffin/laureth-7 | 1.5 | — | 2 | 2.5 | 2 |
| Sodium acrylate/sodium acryloyldimethyl taurate copolymer/isohexadecane/polysorbate 80 | — | 3 | — | — | — |
| Additional Ingredients: | | | | | |
| Dimethicone/dimethiconol | — | 1 | 2 | 0.5 | 2 |
| Fragrance | — | 0.1 | 0.1 | 0.1 | 0.1 |
| Ursolisomes[3] | 3 | — | — | 1 | — |
| Polymethylsilsequioxane | — | — | 0.25 | — | 1 |
| Nylon-12 | — | 0.5 | — | — | — |
| Prestige Silk Violet[4] | — | — | — | — | 1 |
| Timiron Splendid Red[5] | — | 1.0 | — | 2 | — |
| Total: | 100% | 100% | 100% | 100% | 100% |

[1]Available from Kobo products
[2]Palmitoyl-lysine-threonine-threonine-lysine-serine available from Sederma
[3]Ursolisomes are ursolic acid-containing liposomes available from Coletica
[4]Titanium dioxide coated mica violet interference pigment available from Eckart
[5]Silica and titanium dioxide coated mica red interference pigment available from Rona In a suitable vessel, combine the water phase ingredients and heat to 75° C. In a separate suitable vessel, combine the oil phase ingredients and heat to 75° C. Add the oil phase to the water phase and the resulting emulsion is milled (eg., with a Tekmar T-25). Add the thickener to the emulsion. Cool the emulsion to 45° C. while stirring. Upon the mixture cooling to 45° C., add the remaining ingredients. Cool the product with stirring to 30° C. and pour into suitable containers.

Examples 6-11

Moisturizing water-in-silicone creams/lotions are prepared by conventional methods from the following components:

| | Example 6 | Example 7 | Example 8 | Example 9 | Example 10 | Example 11 |
|---|---|---|---|---|---|---|
| Water Phase: | | | | | | |
| Water | qs | qs | qs | qs | qs | qs |
| Glycerin | 3 | 5 | 7 | 10 | 15 | 10 |
| Disodium EDTA | 0.1 | 0.1 | 0.05 | 0.1 | 0.1 | 0.1 |
| Niacinamide | 2 | 0.5 | 3.5 | 3 | 5 | 3 |
| D-panthenol | 0.5 | 0.1 | 1.0 | 0.5 | 1.5 | 0.5 |
| FD&C Red #40 | — | — | — | — | 0.0010 | — |
| FD&C Yellow #5 | — | — | — | — | 0.0005 | — |
| GLW75CAP-MP (75% aq. TiO2 dispersion)[1] | — | 0.4 | — | — | — | — |
| Hexamidine isethionate | 0.1 | 0.1 | — | 1.0 | — | — |
| Palmitoyl-pentapeptide[2] | — | — | — | — | 0.0003 | — |
| N-acetyl glucosamine | 2 | — | 2 | — | 5 | — |
| Silicone/Oil Phase: | | | | | | |
| Cyclomethicone D5 | 10 | 5 | 5 | 10 | 7.5 | 10 |
| Dow Corning 9040 silicone elastomer[3] | — | 10 | 5 | 5 | 7.5 | 5 |
| KSG-15AP silicone Elastomer[4] | 5 | — | 5 | 5 | 7.5 | 5 |
| Dimethione/dimethiconol | — | 2 | 2 | 1 | 2 | 1 |
| Dimethicone 50 csk | 1 | — | — | — | — | — |
| Phytosterol | — | — | — | 0.1 | — | 0.1 |
| Vitamin E Acetate | — | 0.5 | 0.1 | 0.1 | — | 0.1 |
| Thickener: | | | | | | |
| Polyacrylamide/C13-14 isoparaffin/laureth-7 | 2.5 | 2.5 | | — | — | 3 |
| Sodium acrylate/sodium acryloyldimethyl taurate copolymer/isohexadecane/polysorbate 80 | — | — | — | 3 | — | — |
| Acrylates/C10-30 alkyl acrylates crosspolymer | — | — | 0.6 | — | 0.5 | — |
| Dipalmitoyl Hydroxy-Proline Premix: | | | | | | |
| Water | 8.8 | 17.5 | 8.85 | 4.4 | 8.8 | 4.4 |
| Triethanolamine | 0.2 | 0.5 | 0.15 | 0.1 | 0.2 | 0.1 |
| Dipalmitoylhyroxy proline | 1 | 1 | 1 | 0.5 | 2 | 1.0 |
| Additional Ingredients: | | | | | | |
| Fragrance | — | 0.1 | 0.1 | 0.1 | 0.1 | 0.1 |
| Triethanolamine | — | — | — | — | 0.6 | — |
| Ursolisomes[5] | — | — | — | 1 | — | — |
| PTFE | — | 0.5 | — | — | — | — |

-continued

|  | Example 6 | Example 7 | Example 8 | Example 9 | Example 10 | Example 11 |
|---|---|---|---|---|---|---|
| Polymethylsilsequioxane | — | 0.5 | 1.0 | — | — | — |
| Polyethylene | — | 0.5 | — | — | 1.0 | — |
| Flamenco Summit Green G30D[6] | — | — | 1.0 | — | — | — |
| Prestige Silk Red[7] | — | — | — | 1.0 | 1.0 | 1.0 |
| Total: | 100% | 100% | 100% | 100% | 100% | 100% |

[1]GLW75CAP-MP, 75% aqueous titanium dioxide dispersion from Kobo
[2]Palmitoyl-lysine-threonine-threonine-lysine-serine available from Sederma
[3]A silicone elastomer dispersion from Dow Corning Corp
[4]A silicone elastomer dispersion from Shin Etsu,
[5]Ursolisomes are ursolic acid-containing liposomes available from Coletica
[6]Titanium dioxide and tin oxide coated mica green interference pigment from Engelhard
[7]Titanium dioxide coated mica red interference pigment from Eckart In a suitable vessel, combine and mix the water phase ingredients until uniform. In a separate suitable container, combine and mix the silicone/oil phase ingredients until uniform. Separately, prepare the dipalmitoyl hydroxyproline premix by combining the premix ingredients in a suitable container, heating to about 70° C. while stirring, and cooling to room temperature while stirring. Add half the thickener and then the silicone/oil phase to the water phase and mill the resulting emulsion (eg., with a Tekmar T-25). Add the remainder of the thickener, the dipalmitoyl hydroxyproline premix, and then the remaining ingredients to the emulsion while stirring. Once the composition is uniform, pour the product into suitable containers.

Examples 12-17

Moisturizing water-in-silicone creams/lotions are prepared by conventional methods from the following components:

| Component | Example 12 | Example 13 | Example 14 | Example 15 | Example 16 | Example 17 |
|---|---|---|---|---|---|---|
| Phase A | | | | | | |
| water | qs | qs | qs | qs | qs | qs |
| allantoin | 0.2000 | 0.2000 | 0.2000 | 0.2000 | 0.2000 | 0.2000 |
| disodium EDTA | 0.1000 | 0.1000 | 0.1000 | 0.1000 | 0.1000 | 0.1000 |
| ethyl paraben | 0.2000 | 0.2000 | 0.2000 | 0.2000 | 0.2000 | 0.2000 |
| propyl paraben | 0.1000 | 0.1000 | 0.1000 | 0.1000 | 0.1000 | 0.1000 |
| BHT | 0.0150 | 0.0150 | 0.015 | 0.0150 | 0.0150 | 0.015 |
| dexpanthenol | 1.0000 | 0.5000 | 1.0000 | 1.0000 | 1.0000 | 1.0000 |
| glycerin | 7.5000 | 10.0000 | 15.0000 | 7.5000 | 5.0000 | 15.0000 |
| hexamidine isethionate | 0.2000 | 0.1000 | 0 | 0.5000 | 1.0000 | 0 |
| niacinamide | 2.0000 | 3.5000 | 5.0000 | 2.0000 | 2.0000 | 5.0000 |
| palmitoyl-pentapeptide* | 0 | 0 | 0 | 0.0004 | 0.0003 | 0 |
| Phenylbenzimidazole sulfonic acid | 0 | 0 | 0 | 0 | 1.0000 | 0 |
| benzyl alcohol | 0.2500 | 0.2500 | 0.2500 | 0.2500 | 0.2500 | 0.2500 |
| triethanolamine | 0 | 0 | 0 | 0 | 0.6000 | 0 |
| green tea extract | 1.0000 | 1.0000 | 1.0000 | 1.0000 | 1.0000 | 1.0000 |
| N-acetyl glucosamine | 5.0000 | 0 | 5.0000 | 5.0000 | 5.0000 | 0 |
| sodium metabisulfite | 0.1000 | 0.1000 | 0.1000 | 0.1000 | 0.1000 | 0.1000 |
| Phase B | | | | | | |
| cyclopentasiloxane | 15.0000 | 15.0000 | 18.0000 | 15.0000 | 15.0000 | 18.0000 |
| titanium dioxide | 0.5000 | 0.5000 | 0.7500 | 0.5000 | 0.5000 | 0.7500 |
| Phase C | | | | | | |
| C12-C15 alkyl benzoate | 1.5000 | 0 | 0 | 1.5000 | 1.5000 | 0 |
| vitamin E acetate | 0.5000 | 0 | 1.0000 | 0.5000 | 0.5000 | 1.0000 |
| retinyl propionate | 0.3000 | 0 | 0 | 0.2000 | 0.2000 | 0 |
| phytosterol | 2.0000 | 0 | 0 | 5.0000 | 3.0000 | 0 |
| Phase D | | | | | | |
| KSG-21 silicone elastomer[1] | 4.0000 | 4.0000 | 5.0000 | 4.0000 | 4.0000 | 5.0000 |

-continued

| Component | Example 12 | Example 13 | Example 14 | Example 15 | Example 16 | Example 17 |
|---|---|---|---|---|---|---|
| Dow Corning 9040 silicone elastomer[2] | 15.0000 | 15.0000 | 12.0000 | 15.0000 | 15.0000 | 12.0000 |
| Abil EM-97 Dimethicone Copolyol[3] | 0.5000 | 0 | 0 | 0.5000 | 0.5000 | 0 |
| polymethylsilsesquioxane | 2.5000 | 2.5000 | 2.0000 | 2.5000 | 2.5000 | 2.0000 |
| fragrance | 0.2000 | 0.2000 | 0.2000 | 0.2000 | 0.2000 | 0.2000 |
| Phase E | | | | | | |
| Water | 8.8 | 17.5 | 8.85 | 4.4 | 8.8 | 8.85 |
| Triethanolamine | 0.2 | 0.5 | 0.15 | 0.1 | 0.2 | 0.15 |
| Dipalmitoylhyroxy proline | 1 | 2 | 1 | 0.5 | 1 | 1 |

[1]KSG-21 is an emulsifying silicone elastomer available from Shin Etsu
[2]A silicone elastomer dispersion from Dow Corning Corp
[3]Abil EM-97 available from Goldschmidt Chemical Corporation In a suitable vessel, blend the Phase A components together with a suitable mixer (e.g., Tekmar model RW20DZM) and continue mixing to dissolve all of the components. Then, blend the Phase B components together in suitable vessel and mill using a suitable mill (e.g., Tekmar RW-20) for about 5 minutes. Add the Phase C components to the Phase B mixture with mixing. Then, add the Phase D components to the mixture of Phases B and C and then mix the resulting combination of Phase B, C and D components using a suitable mixer (e.g., Tekmar RW-20) for about 1 hour. Then prepare Phase E is by combining all ingredients, heating the ingredients to 70° C. while stirring, and cooling back to room temperature while stirring. Add Phase E to Phase A while mixing. Next, slowly add Phase A is to the mixture of Phases B, C and D with mixing. Mix the resulting mixture is continually until the product is uniform. Then mill the resulting product for about 5 minutes using an appropriate mill (e.g., Tekmar T-25).

What is claimed is:

1. Skin care compositions for regulating the condition of mammalian keratinous tissue comprising:
   a) at least 0.01%, by weight of the composition, of a dipalmitoyl hydroxyproline salt wherein the dipalmitoryl hydroxyproline salt is a triethanolamine salt;
   b) a safe and effective amount of a skin care active selected from the group consisting of sugar amines, its salts and its derivatives, a hexamidine compound conforming to the structure:

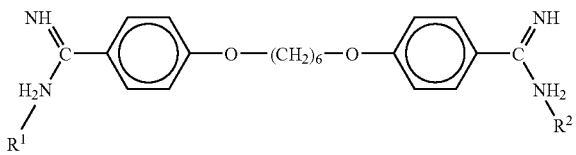

wherein $R^1$ and $R^2$ comprise organic acids, and mixtures thereof; and
   c) a dermatologically acceptable carrier.

2. The skin care composition of claim 1 wherein the weight ratio of a) to b) is from about 1:12 to about 1:0.1.

3. The skin care composition of claim 1 wherein said composition comprises from about 0.1% to about 10%, by weight of the composition, of said dipalmitoyl hydroxyproline salt.

4. The skin care composition of claim 3 wherein said dipalmitoyl hydroxyproline salt comprises from about 0.1 to 2% by weight of the composition.

5. The skin care composition of claim 1 wherein said skin care active comprises said sugar amines, its salts at a level from about 0.1% to about 10.0% by weight of the compositions.

6. The skin care composition of claim 5 wherein said sugar amine is N-acetyl D-glucosamine.

7. The skin care composition of claim 1 wherein said skin care active comprises said hexamidine compounds comprising from about 0.001 to 10.0% by weight of the composition.

8. The skin care composition of claim 7 wherein said hexamidine compound is diisethionate hexamidine.

9. The skin care composition of claim 1 wherein said skin care active comprises a combination of said sugar amines, its salts and said hexamidine compounds.

10. The skin care composition of claim 9 wherein said sugar amines, its salt and its derivatives if from about 0.1% to about 10.0% and said hexamidine compound is from about 0.1% to about 10.0% by weight of the composition.

11. The skin care composition of claim 9 wherein said sugar amine is N-acetyl D-glucosamine and said hexamidine compound is diisethionate hexamidine.

12. The skin care composition of claim 1 wherein said composition comprises from about 0.0001% to about 10%, by weight of the composition, of an additional skin care active selected from the group consisting of desquamatory actives, anti-acne actives, wrinkle repair actives, anti-oxidants, radical scavengers, chelators, anti-inflammatory agents, topical anesthetics, tanning actives, skin lightening agents, anti-cellulite agents, flavonoids, antimicrobial actives, antifungal actives, sunscreen actives, conditioning agents, and combinations thereof.

13. The skin care composition of claim 12 wherein the skin care active is selected from the group consisting of Vitamin $B_3$, its salts; retinoids; peptides; phytosterol and combinations thereof.

14. The skin care composition of claim 1 wherein the composition has a pH from about 4 to about 8.

15. The skin care composition of claim 1 wherein said composition is an emulsion.

16. A process for making the composition of claim 1 wherein the salt of the dipalmitoyl hydroxyproline is formed during the processing of said composition, said process comprising adding a sufficient amount of a basic reagent at a concentration sufficient to convert said dialkanoyl hydroxyproline compound into a desired level of its corresponding salt.

17. A method of regulating the condition of mammalian keratinous tissue, said method comprising the step of topically applying to a treatment surface of the body in need of such treatment the composition of claim 1.

18. The method according to claim 17 wherein the condition to be regulated is selected from the group consisting of thickening the skin; reducing skin atrophy, spider vessels, the appearance of red blotchiness on the skin, the appearance of dark under-eye circles, puffy eyes, sallowness of skin, pore size of skin, oily appearance of skin shiny appearance of skin, hyperpigmentation of skin, sagging of skin, fine lines and wrinkles; reducing dryness of keratinous tissue, reducing itching of skin, reducing the roughness of skin; and combinations thereof.

19. Skin care compositions for regulating the condition of mammalian keratinaus tissue comprising:
   a) at least 0.01% by weight of a dipalmitoyl hydroxyproline salt, wherein the dipalmitoyl hydroxyproline salt is a triethanolamine salt
   b) a safe and effective amount of a sugar amine, its salts and;
   c) a safe and effective amount of a hexamidine compound conforming to the structure;

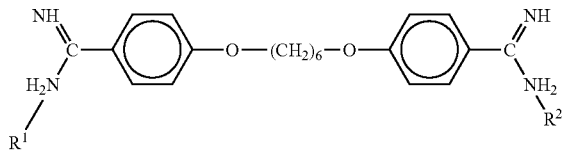

wherein $R^1$ and $R^2$ comprise organic acids; and
   d) a dermatologically acceptable carrier.

20. The skin care composition of claim 19 wherein said composition comprises from about 0.1% to about 10.0%, by weight of the composition, of said sugar amine, its salt, and from about 0.1% to about 10.0%, by weight of the composition, of said hexarnidine.

21. The skin care composition of claim 19 wherein said sugar amine is N-acetyl D-glucosamine and said hexamidine compound is diisethionaxe hexamidine.

* * * * *